(12) United States Patent
Tzakis et al.

(10) Patent No.: US 8,448,833 B2
(45) Date of Patent: May 28, 2013

(54) STAPLING APPARATUS FOR PERFORMING ANASTOMOSIS ON HOLLOW ORGANS

(75) Inventors: Andreas Tzakis, Miami, FL (US);
James Morelli, Southington, CT (US);
Daniel Sadowski, Kensington, CT (US)

(73) Assignee: Zakease Surgical Inc., Miami, FL (US)

( * ) Notice: Subject to any disclaimer, the term of this patent is extended or adjusted under 35 U.S.C. 154(b) by 234 days.

(21) Appl. No.: 12/803,903

(22) Filed: Jul. 9, 2010

(65) Prior Publication Data
US 2011/0180584 A1 Jul. 28, 2011

Related U.S. Application Data

(63) Continuation-in-part of application No. 12/657,696, filed on Jan. 26, 2010, now Pat. No. 8,245,897.

(51) Int. Cl.
*A61B 17/115* (2006.01)
(52) U.S. Cl.
USPC .......................................... 227/181.1; 227/19
(58) Field of Classification Search
USPC ............................ 227/175.1, 176.1, 181.1, 19
See application file for complete search history.

(56) References Cited

U.S. PATENT DOCUMENTS

| 3,144,654 | A | * | 8/1964 | Mallina et al. ................ 227/19 |
| 3,973,709 | A | * | 8/1976 | Akopov et al. ................ 227/19 |
| 4,216,890 | A | * | 8/1980 | Akopov et al. ................ 227/22 |
| 4,466,436 | A | * | 8/1984 | Lee ............................. 227/179.1 |
| 4,821,939 | A | * | 4/1989 | Green ........................... 227/19 |
| 5,163,943 | A | * | 11/1992 | Mohiuddin et al. ........ 606/118 |
| 6,905,504 | B1 | * | 6/2005 | Vargas ......................... 606/153 |
| 6,942,675 | B1 | * | 9/2005 | Vargas ......................... 606/153 |
| 2007/0027473 | A1 | * | 2/2007 | Vresh et al. ................ 606/219 |
| 2007/0208359 | A1 | | 9/2007 | Hoffman |

FOREIGN PATENT DOCUMENTS

GB 2108418 A * 5/1983

* cited by examiner

*Primary Examiner* — M. Alexandra Elve
*Assistant Examiner* — Andrew M Tecco
(74) *Attorney, Agent, or Firm* — Carothers & Carothers

(57) ABSTRACT

A stapling apparatus for performing anastomosis on hollow organs which includes an adjacent aligned pair of stapling jaws for respectively retaining hollow organ ends together in aligned registration for stapling the ends together to form an anastomosis. Each of the stapling jaws has opposing hinged hemostat jaws operable for clamping respective hollow organ ends therebetween prior to stapling. The hemostat jaws include a stapling mechanism for stapling the retained hollow organ ends together.

4 Claims, 22 Drawing Sheets

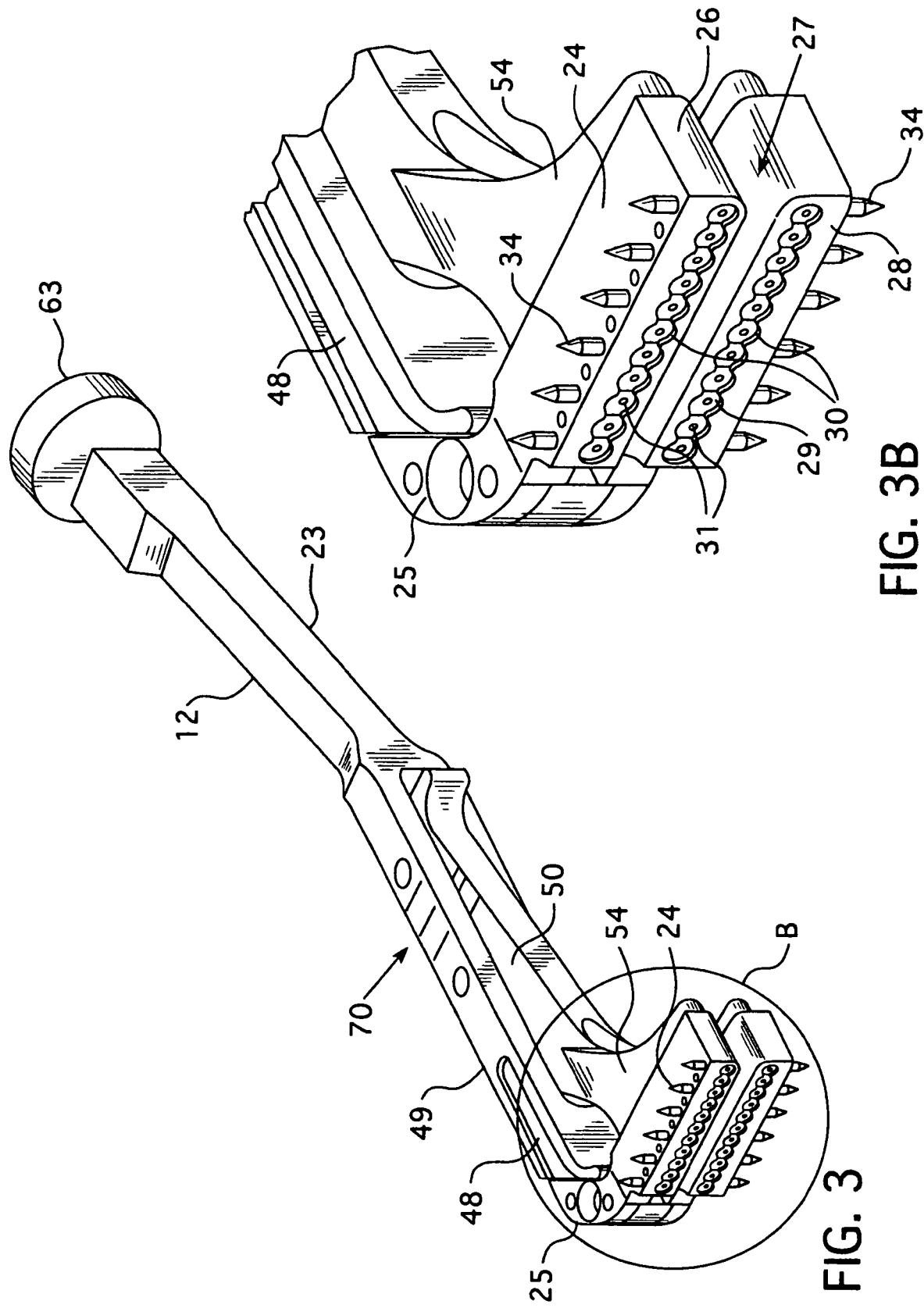

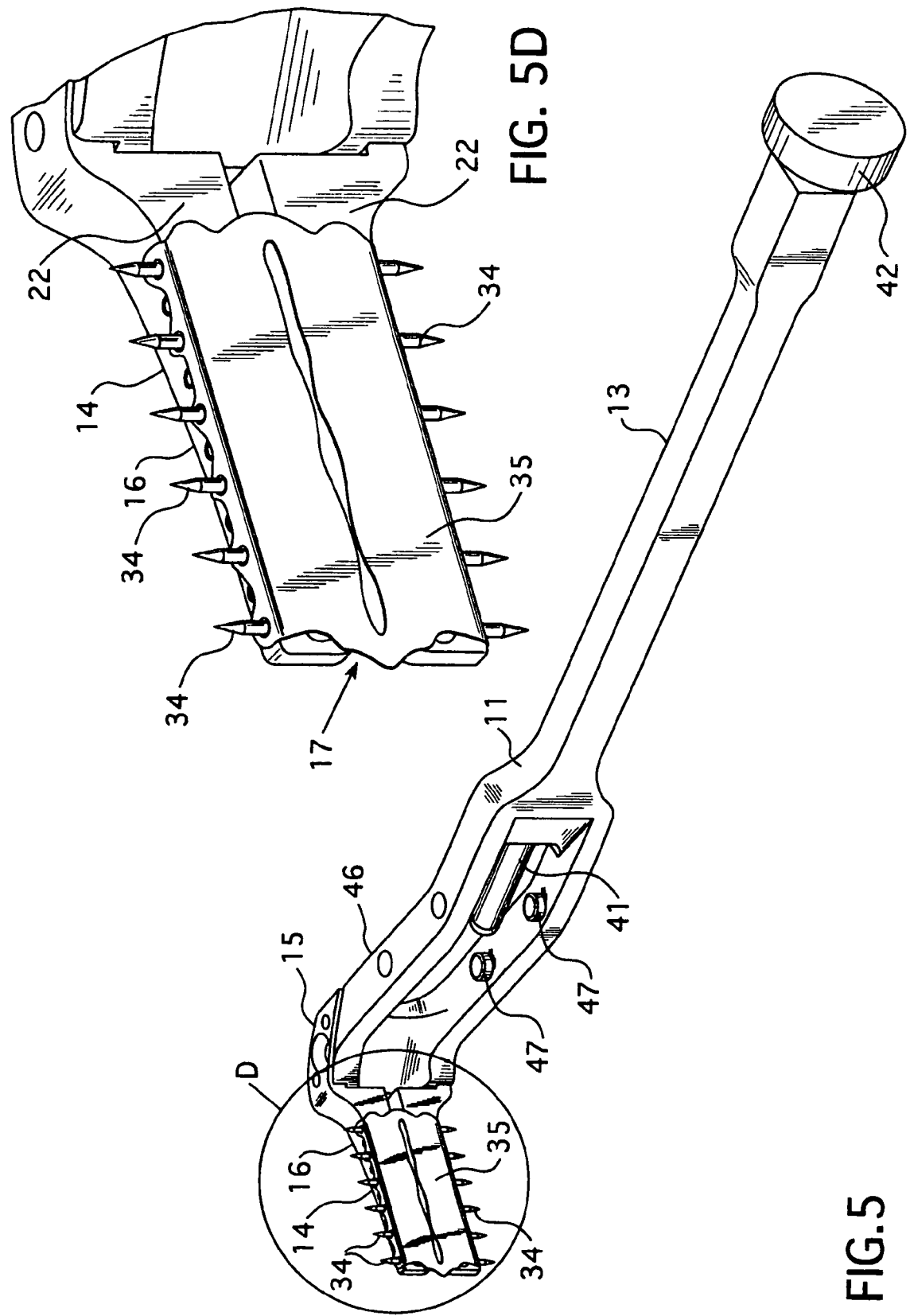

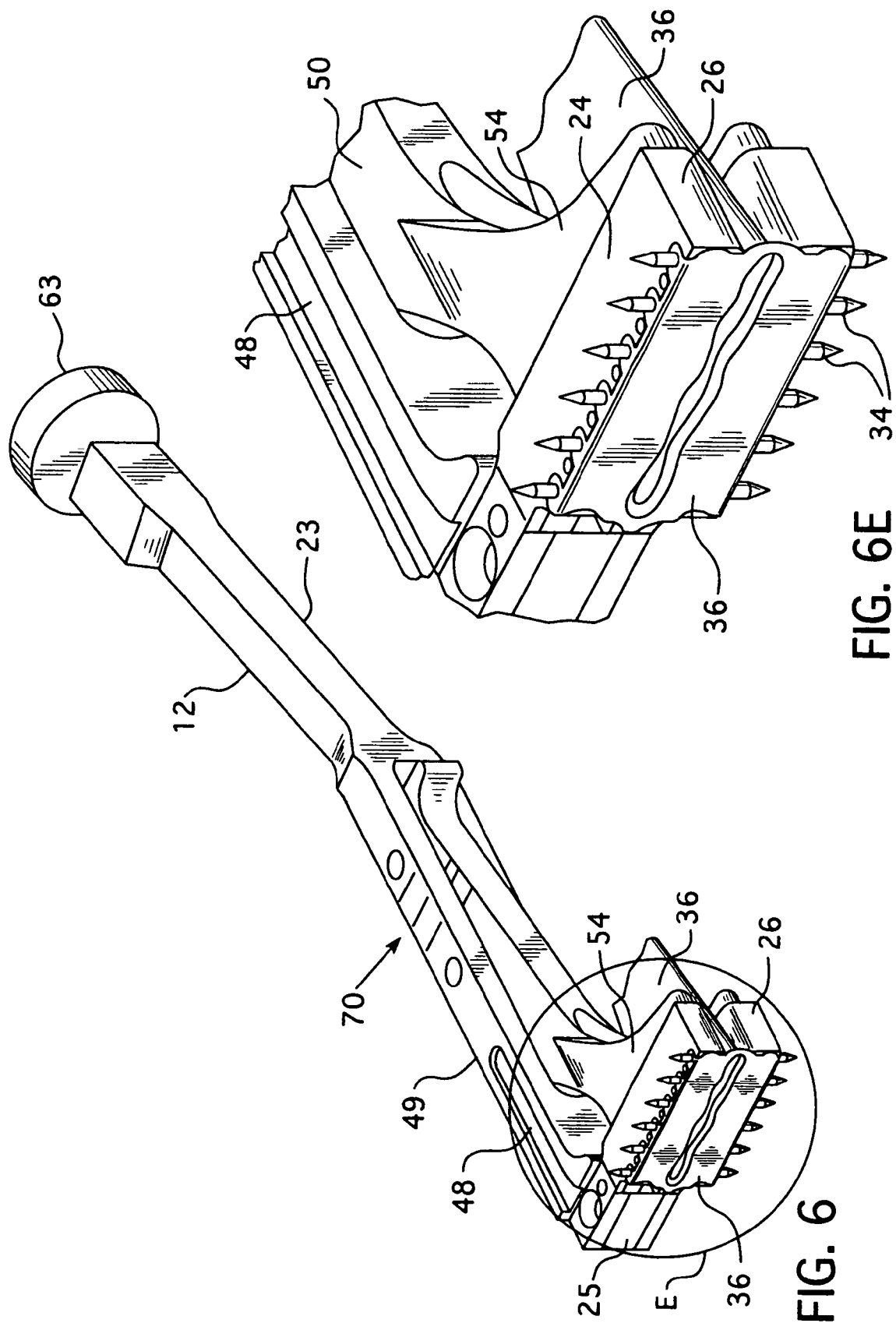

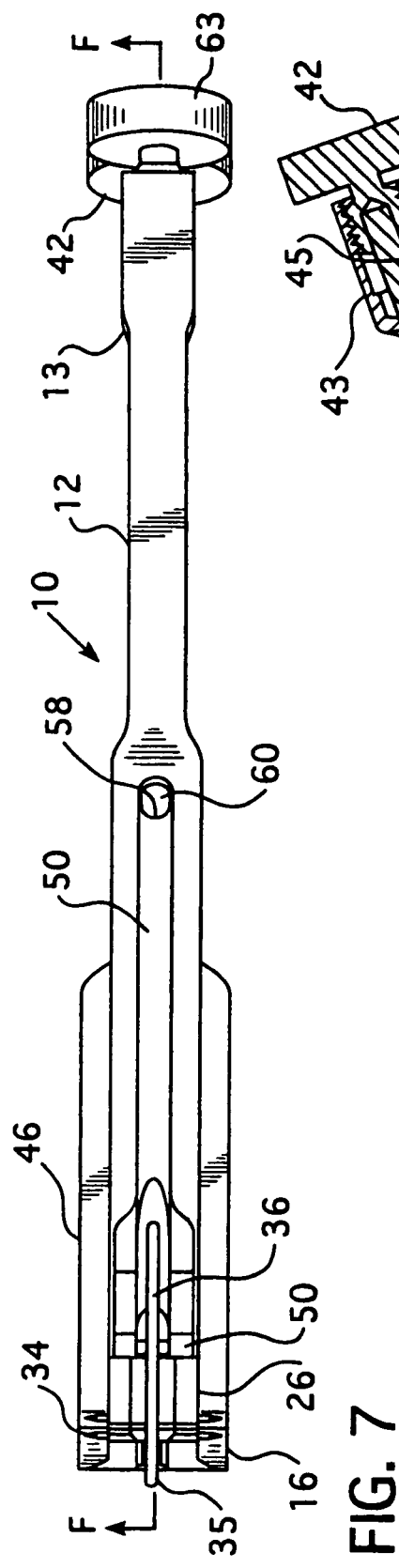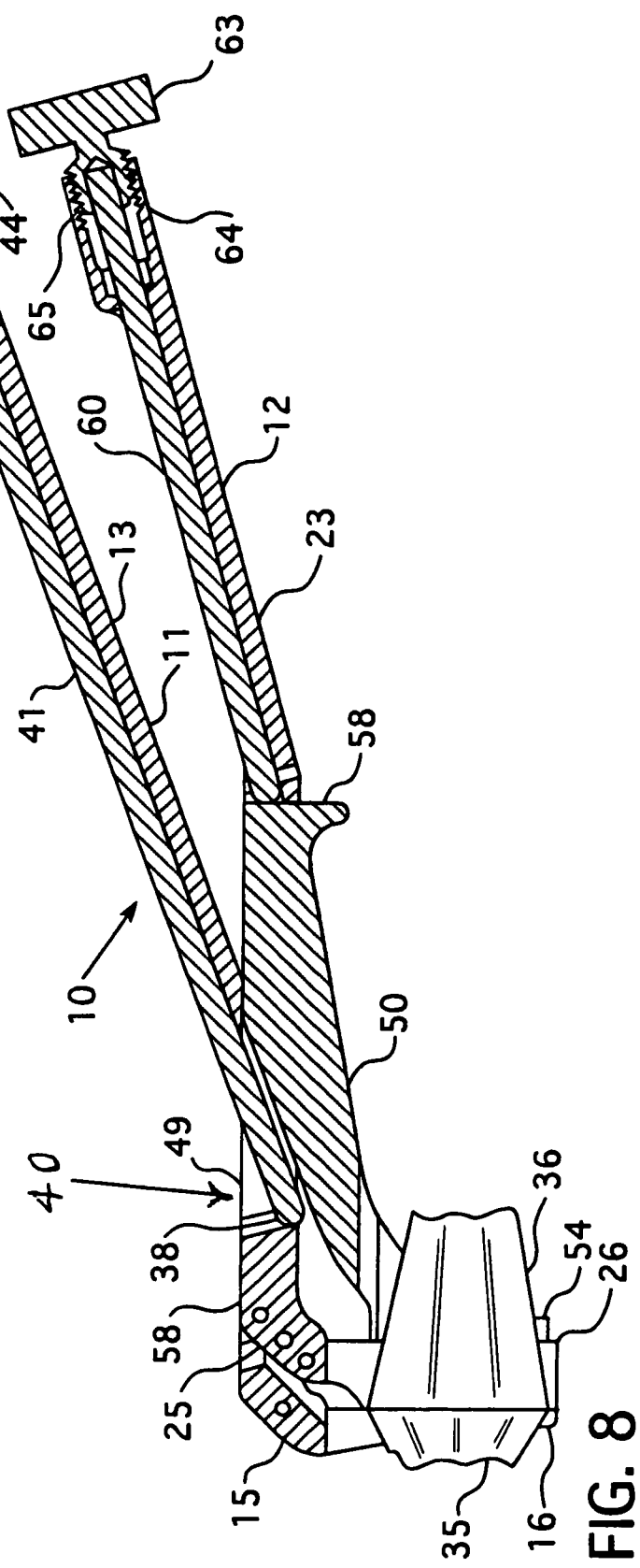

STAPLING APPARATUS FOR PERFORMING ANASTOMOSIS ON HOLLOW ORGANS

CROSS REFERENCE

This application is a continuation-in-part of U.S. patent application Ser. No. 12/657,696, filed Jan. 26, 2010 now U.S. Pat. No. 8,245,897, having the same title.

FIELD OF THE INVENTION

The present invention pertains to the field of medicine and more particularly to surgery. More specifically, the present invention generally relates to surgical suturing devices and methods for applying anastomosis onto hollow organs, eg. the organs of the digestive tract or blood vessels, for instance, for joining them together in end-to-end or end-to-side utilizing fastener securing techniques.

BACKGROUND OF THE INVENTION

End-to-end anastomosis is a surgical procedure for connecting an end of one hollow organ to an end of another hollow organ. End-to-end anastomosis is commonly performed on vascular and/or visceral tissue. Microvascular anastomosis is generally performed to make ends of blood vessels in the course of, for example, reattaching severed body parts and/or transplanting organs. Microvascular anastomosis is generally performed by hand under a microscope, and is tedious and painstaking work. As a result, it can take many hours to complete just the microvascular anastomosis required to reconnect a severed body part or transplant an organ.

In such surgical procedures, speed of performing the operation can become extremely critical. For example, in transplant surgery, it is very important to reconnect the supply of blood to the transplanted organ as soon as possible in order to minimize damage to the organ. Such blood vessels are now normally anastomosed end-to-end or end-to-side by suturing techniques. Such suture anastomosis procedures generally take the skilled surgeon anywhere from ten to twenty minutes to complete for each anastomosis and for many organs a number of such connections are required.

At the present, there are no known anastomosis stapling or fastener securing devices or techniques for the vascular system which are truly failsafe and foolproof. It is thus a principal object of the present invention to provide such a full proof surgical stapler for automated hollow organ anastomosis which permits full and unobstructed access to the surgical field and provides insured or guaranteed stapling of the hollow organ ends without misfire of any one of the staples. The anastomosis stapler of the present invention accordingly provides ease of use, accessibility to the surgical site, consistency and dependability in operation, all in less time possible with prior art techniques. In addition, the stapler of the present invention is reusable.

SUMMARY OF THE INVENTION

The stapling apparatus of the present invention for performing anastomosis on hollow organs is comprised of an adjacent aligned pair of stapling jaws for respectively retaining hollow organ ends together in aligned registration for stapling the ends together to form an anastomosis. Each of these stapling jaws is comprised of opposing hinged hemostat jaws which are operable for clamping respective hollow organ ends therebetween prior to stapling. The hemostat jaws include a stapling mechanism for stapling the retained hollow organ ends together.

The stapling apparatus of the present invention provides a significant advantage over anastomosis surgical staplers of the prior art in that the stapling mechanism serves not only to staple the hollow organ ends together, but in addition, includes hemostat jaws which make it easier for the surgeon to attach or otherwise preliminarily secure blood vessel or other hollow organ ends to be anastomized to the stapling mechanism, which not only permits fast easy initial securement to the stapling mechanism, but in addition, stops vessel blood flow during the procedure.

The stapler hemostat jaws are provided with a spaced series of pins which extend laterally outward from outer sides of the hemostat jaws for piercing and retaining the respectively clamped hollow organ ends stretched over the stapling mechanism.

The stapling apparatus of the present invention is preferably provided wherein the pair of stapling jaws are separable from each other for guided manipulation into and out of stapling registration. This permits easy attachment of the respective hollow organ ends to be stapled together to the respective separated stapling jaws before they are secured together in stapling registration.

BRIEF DESCRIPTION OF THE DRAWINGS

Other objects and advantages appear hereinafter in the following description and claims. The accompany drawings show, for the purpose of exemplification, without limiting the scope of the invention or appended claims, certain practical embodiments of the present invention wherein:

FIG. 3 is a perspective view of the L-shaped staple retainer tool portion of the stapler of the present invention without the inclusion of a hollow organ end applied thereto;

FIG. 3B is an enlarged view of detail B of the apparatus shown in FIG. 3;

FIG. 5 is a perspective view of the L-shaped clip retainer tool of FIG. 1 with a first hollow organ end to be anastomosed applied thereover prior to combining of the two L-shaped retainer tools for stapling;

FIG. 5D is an enlarged view of the detail D of the L-shaped clip retainer tool shown in FIG. 5;

FIG. 6 is a perspective view of the L-shaped stapler retainer tool portion of the stapler of the present invention with a second hollow organ end to be anastomosed applied thereover;

FIG. 6E is an enlarged view of detail E of the staple retainer tool shown in FIG. 6;

FIG. 7 is a bottom view of the anastomosis stapler of the present invention showing the two L-shaped clip and staple retainer tools combined and clamped together with opposed hollow organ ends applied thereto and coaptating in preparation for stapling;

FIG. 8 is a view in mid cross section of the stapler shown in FIG. 7 as seen along section line F-F with the hollow organ ends to be stapled unsectioned;

DETAILED DESCRIPTION OF THE PREFERRED EMBODIMENTS

Figure 1:
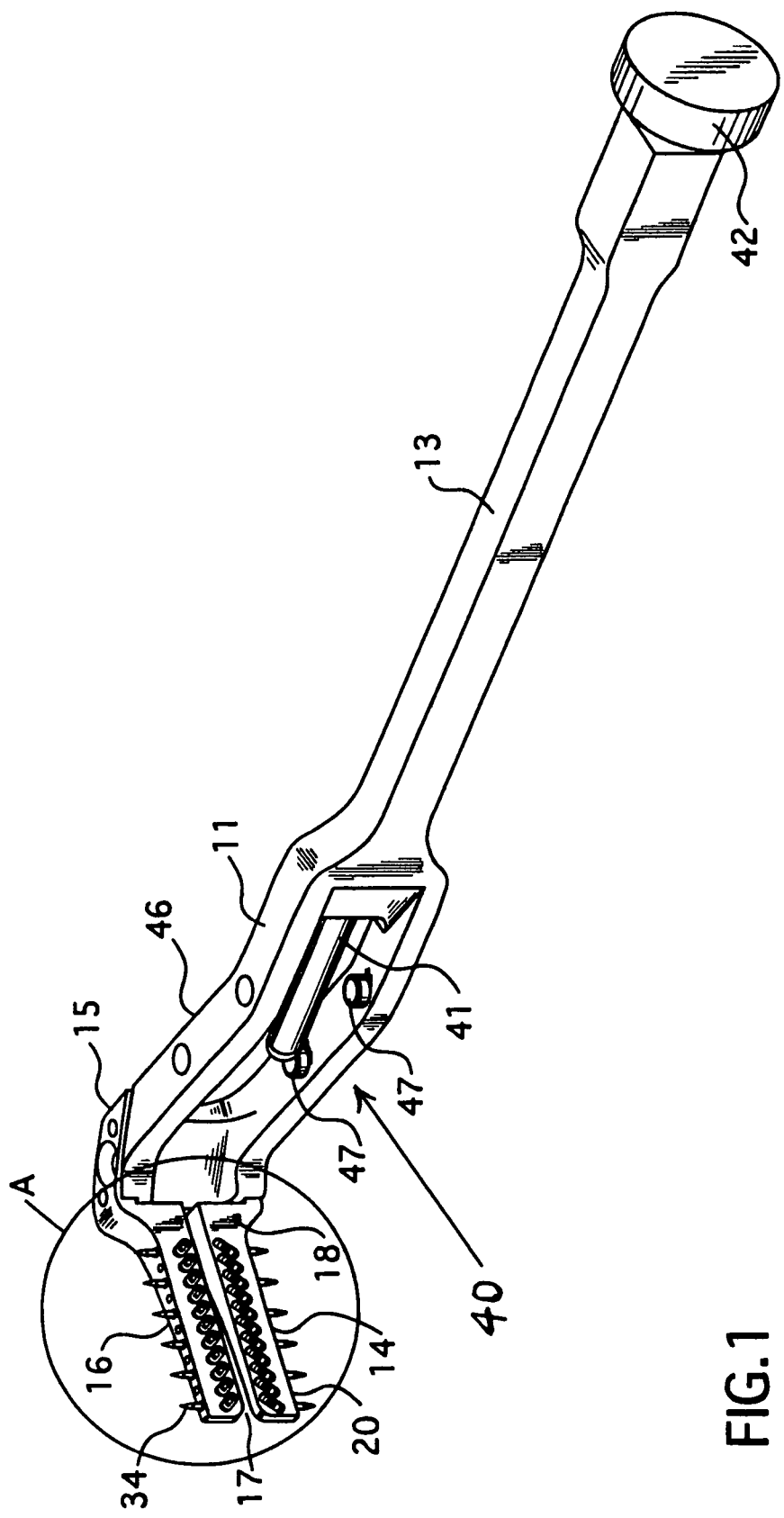
FIG. 1 is a perspective view of the L-shaped clip retainer tool portion of the stapler of the present invention prior to securement thereto of a hollow organ end.
Figure 2:
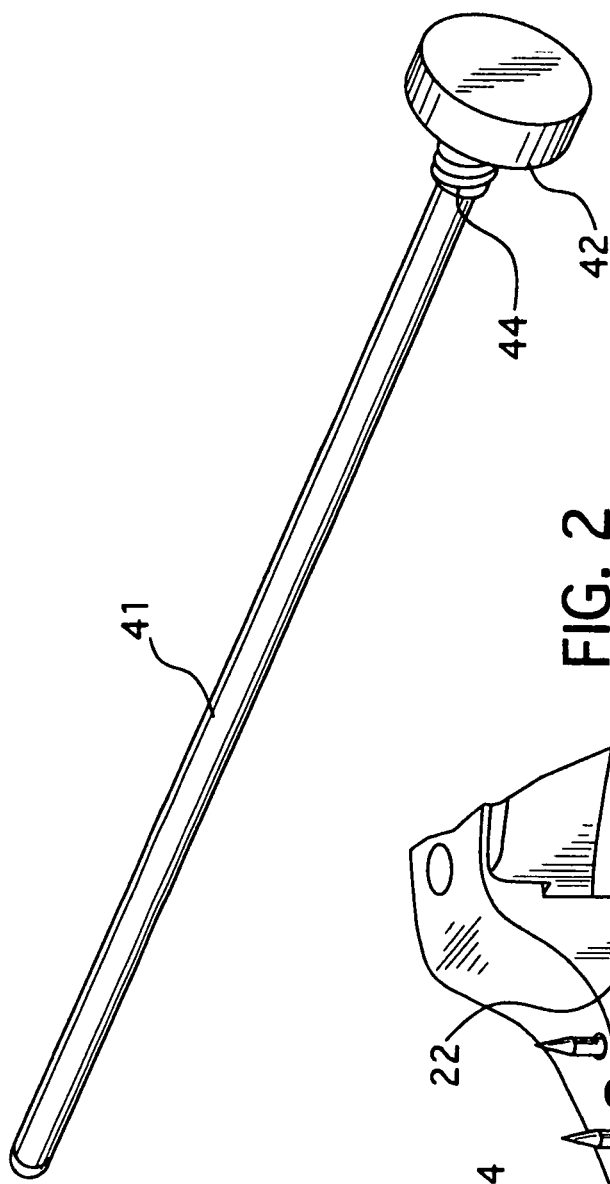
FIG. 2 is a perspective view of the clamping rod removed from the handle of the L-shaped clip retainer tool of FIG. 1.

Referring to FIGS. 1 through 17, the anastomosis stapling apparatus 10 of the present invention is shown in its complete combined form in FIGS. 7 through 14. The stapling apparatus 10 is comprised of two separate combinable tools in the form of L-shaped clip retainer tool 11 and L-shaped staple retainer tool 12. Describing first the L-shaped clip retainer tool 11 shown in FIGS. 1 and 1A, the clip retainer tool 11 includes an elongated clip retainer handle 13 with a clip retaining foot 14 extending laterally from bottom distal end 15 of handle 13. Clip retaining foot 14 is comprised of a C-shaped clip jaw 16 which is positioned in a plane that is substantially transverse to the clip retainer handle 13 as illustrated in FIG. 1. C-shaped clip jaw 16 defines an organ exit gap 17 for removal of stapled hollow organ ends after stapling as will be explained in greater detail hereinafter.

Side face 18 of C-shaped clip jaw 16 provides an upwardly facing top face 22. Clip retainer 20 is provided in clip jaw 16 and has a series of staple receiving and retaining clips 21 received and arranged circumferentially along upwardly facing top face 22 of retainer 20. In this embodiment, clip retainer 20 is an integral part of C-shaped clip jaw 16. However, as will be explained in conjunction with another possible embodiment of the present invention, the clip retainer 20 may be a separate piece which is removably and slidably received in C-shaped jaw 16.

The second tool part of stapling apparatus 10 of the present invention is the L-shaped staple retainer tool 12 illustrated in FIGS. 3 and 3B. L-shaped staple retainer tool 12 includes an elongated staple retainer handle 23 with a staple retaining foot 24 extending laterally from bottom distal end 25 of staple retaining handle 23. Staple retaining foot 24 is comprised of a C-shaped staple jaw 26 which is positioned in a plane substantially transverse to staple retaining handle 23 as illustrated. C-shaped staple jaw 26 defines an organ exit gap 27 and side face 28 thereof provides a downwardly facing bottom face. Staple retainer 29 is provided in staple jaw 26 and has a series of staple sockets 30 arranged circumferentially along the downwardly facing bottom face 28 for retaining a series of staples 31 with their penetrating tips 32 (see FIG. 11) exposed from bottom face 28. As may be viewed more clearly in FIG. 11, the staples 31 are comprised of nails constructed of surgical stainless steel which are each received in seating bushings 33 made of a suitable plastic material, such as TEFLON®.

Figure 1A:
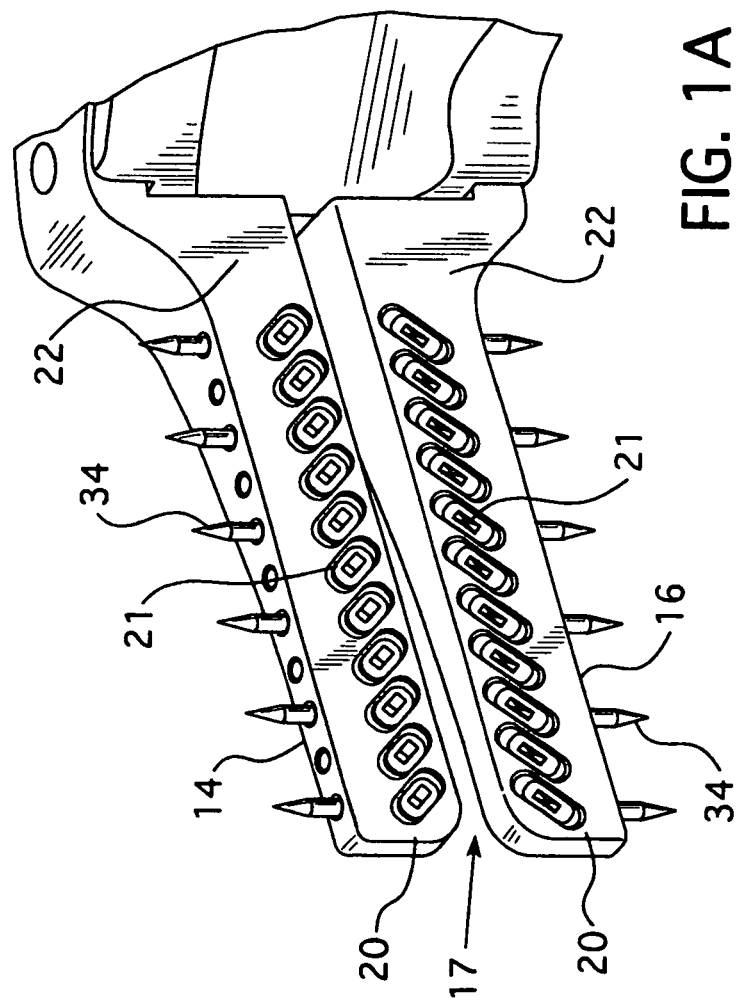
FIG. 1A is an enlarged view showing detail A of FIG. 1.
Figures 4, 4C:
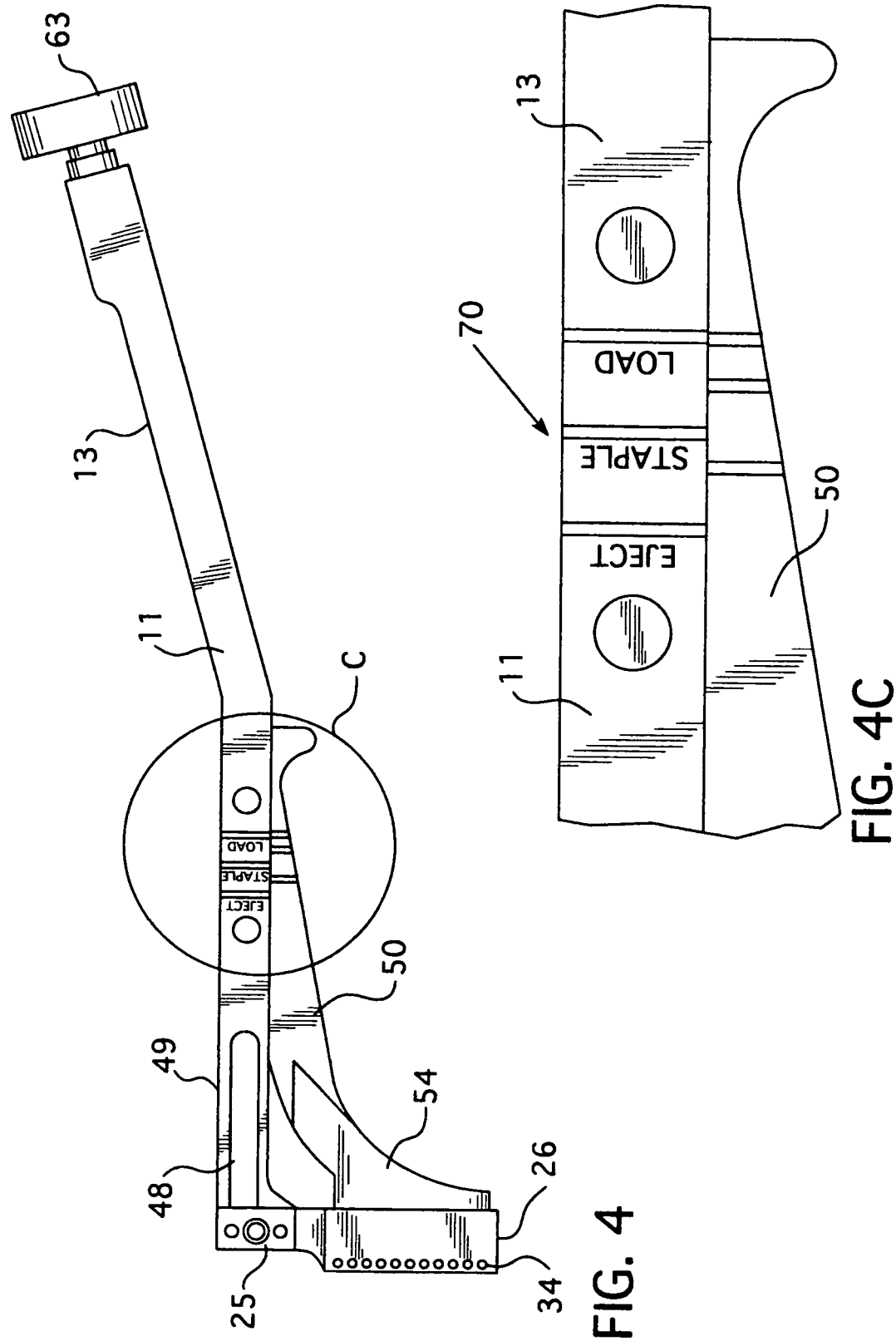
FIG. 4 is a side view of the L-shaped staple retainer tool shown in FIG. 4.
FIG. 4C is an enlarged view of detail C of the tool shown in FIG. 4.
Figure 9:
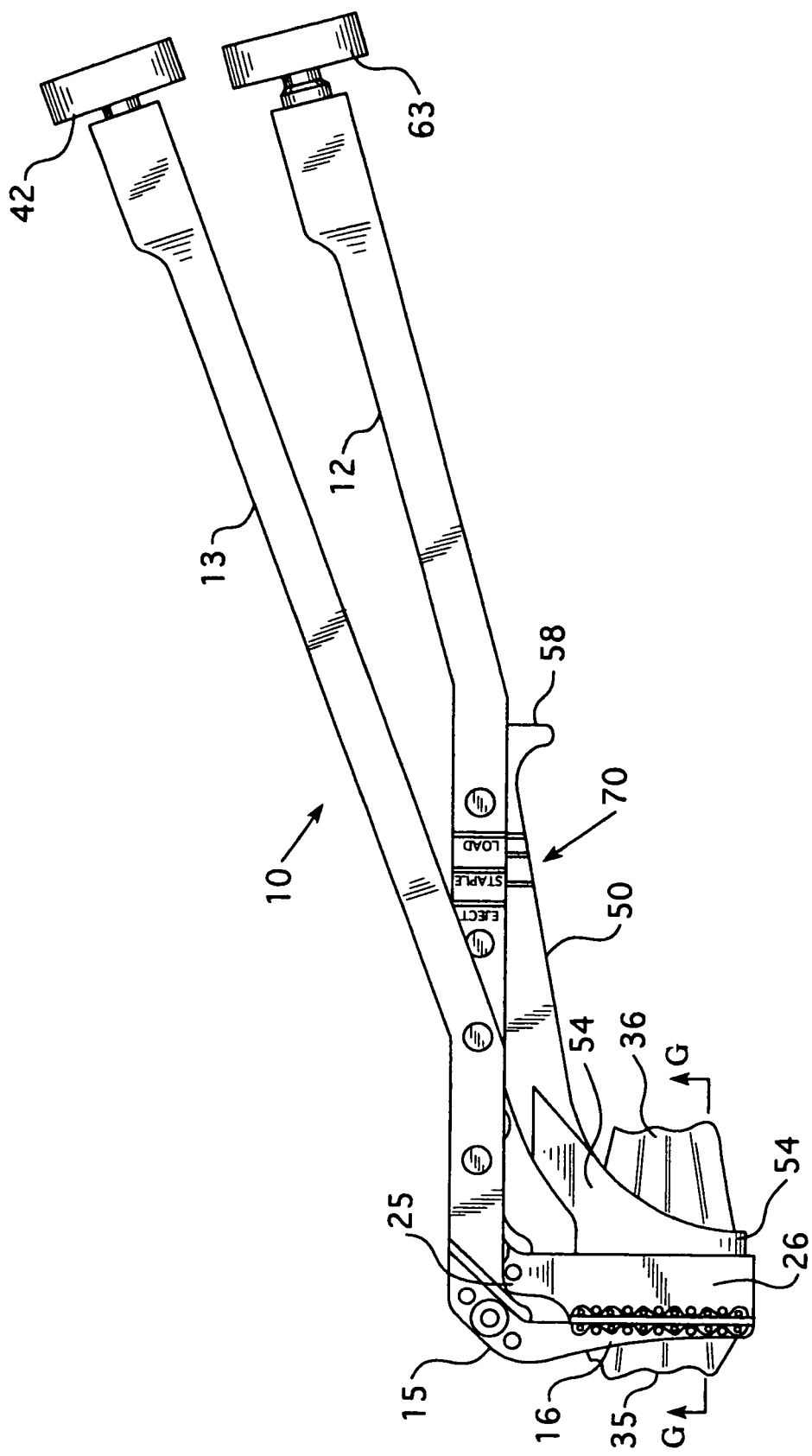
FIG. 9 is a view in side elevation of the stapler shown in FIG. 7 just prior to stapling of the hollow organ ends.

The staple retaining clips 21 of the L-shaped tool 11 as shown in FIGS. 1 and 1A, are metal push nuts made of suitable surgical metal, such as surgical stainless steel. As with conventional push nuts, the clips 21 each have an opening therein to receive the corresponding tips 32 of staples 31, and the clips are provided with opposing metal teeth 37 which engage and grip the nails of staples 31 to prevent removal after penetration.

Referring to FIGS. 1 and 1A, and FIGS. 3 and 3A, a spaced series of pins 34 extend laterally outward from outer sides of the C-shaped jaws 16 and 26. These pins 34 are provided for piercing and retaining respective hollow organ ends 35 and 36 as illustrated in FIGS. 5 and 5B, and 6 and 6E. These hollow organs ends 35 and 36 are illustrated as being secured to L-shaped clip retainer tool 11 and L-shaped staple retainer tool 12 respectively prior to combining of the tools and prior to stapling the hollow organ ends together.

Figure 10:
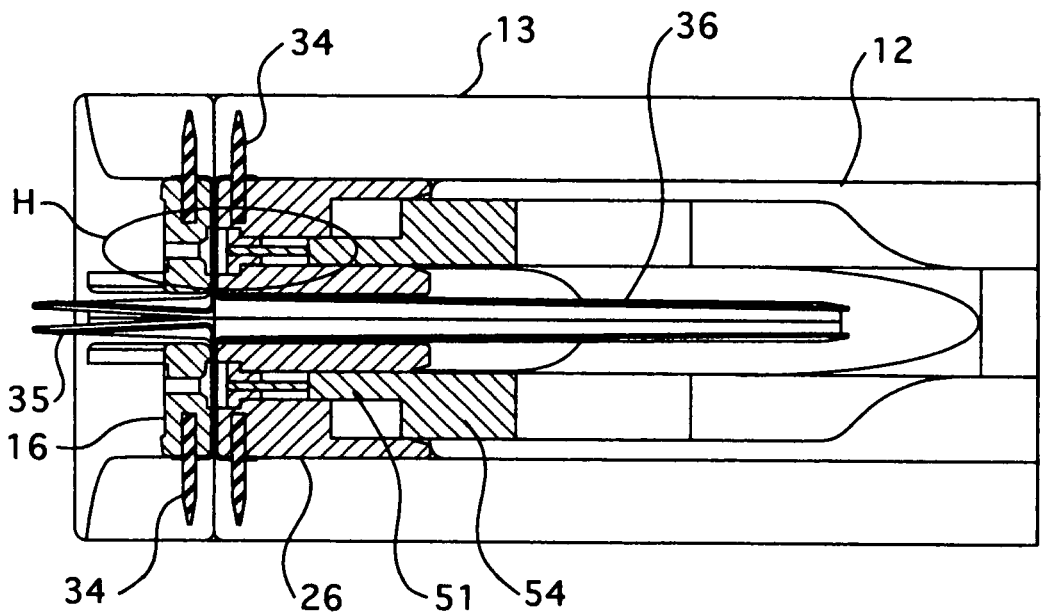
FIG. 10 is an enlarged sectional view of the stapler shown in FIG. 9 as seen along section line G-G.
Figure 11:
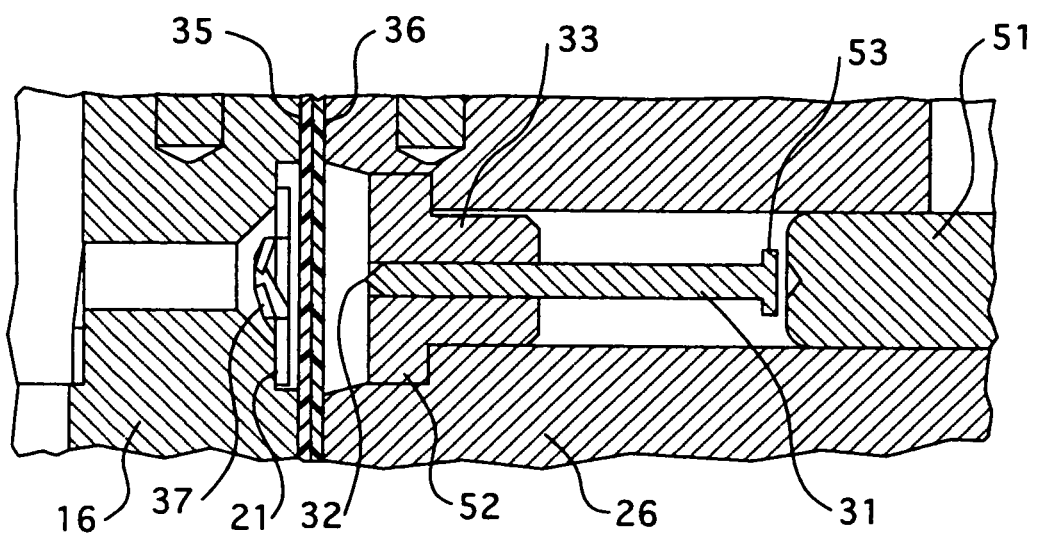
FIG. 11 is an enlarged view of detail H of FIG. 10.
Figure 12:
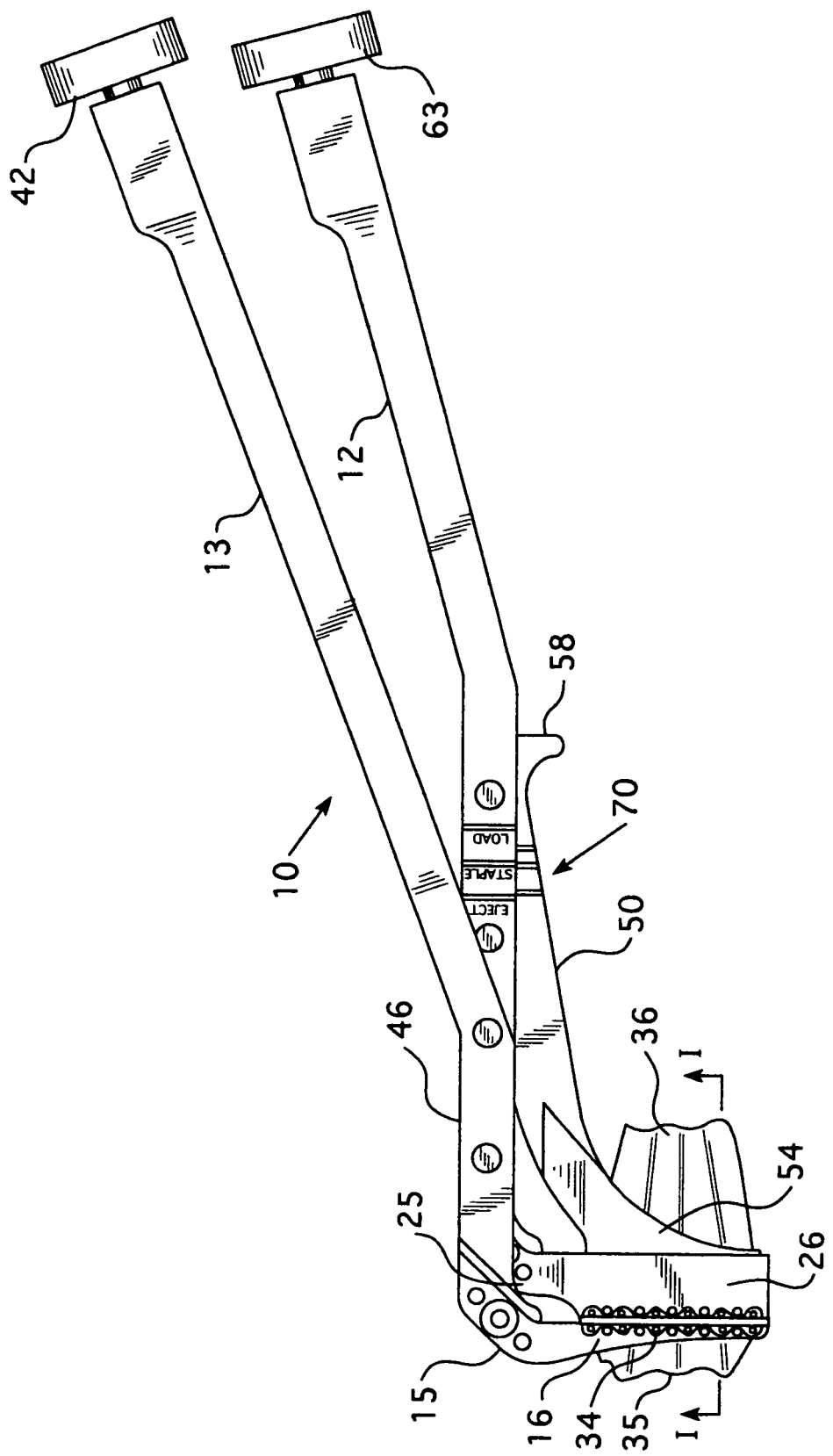
FIG. 12 is a view in side elevation of the anastomosis stapler shown in FIG. 7 subsequent to actuation thereof showing the hollow organ ends stapled together.
Figure 13:
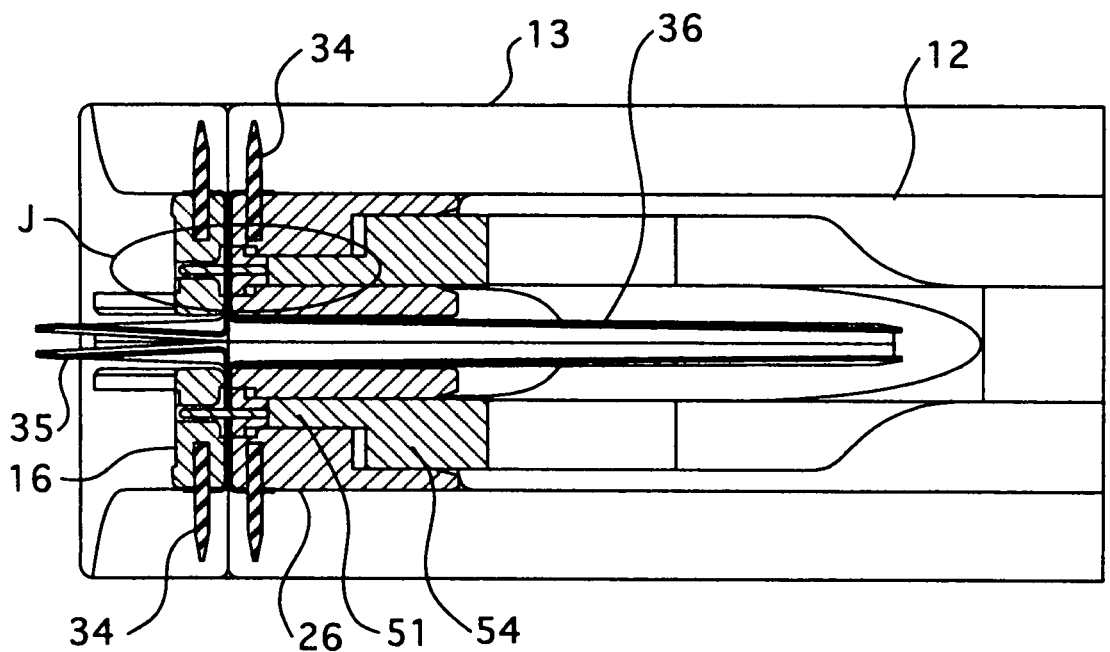
FIG. 13 is an enlarged sectional view of the stapler shown in FIG. 12 as being along section line I-I.
Figure 14:
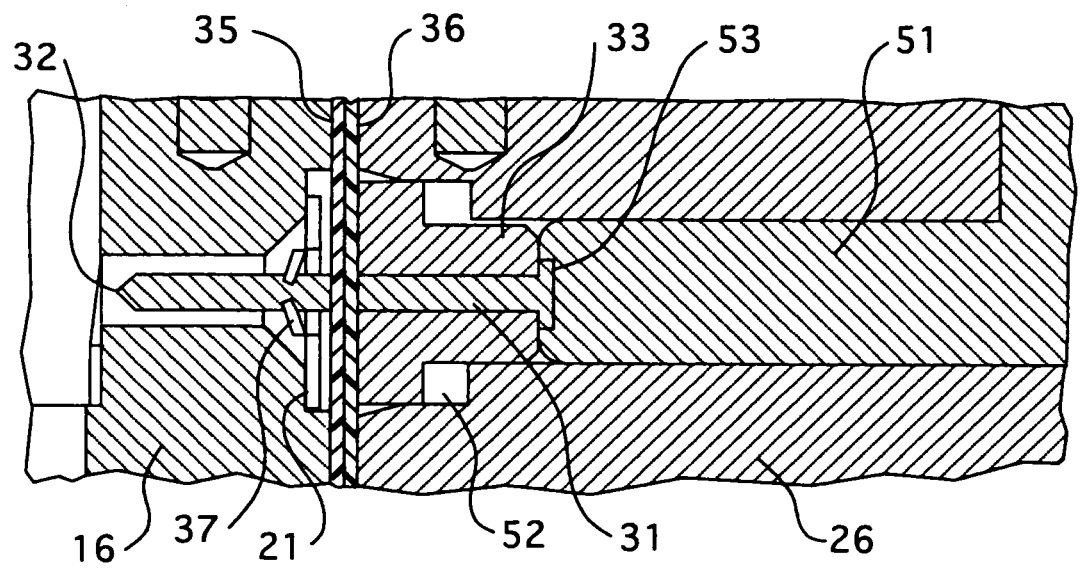
FIG. 14 is an enlarged view of detail J of FIG. 13.
Figure 15:
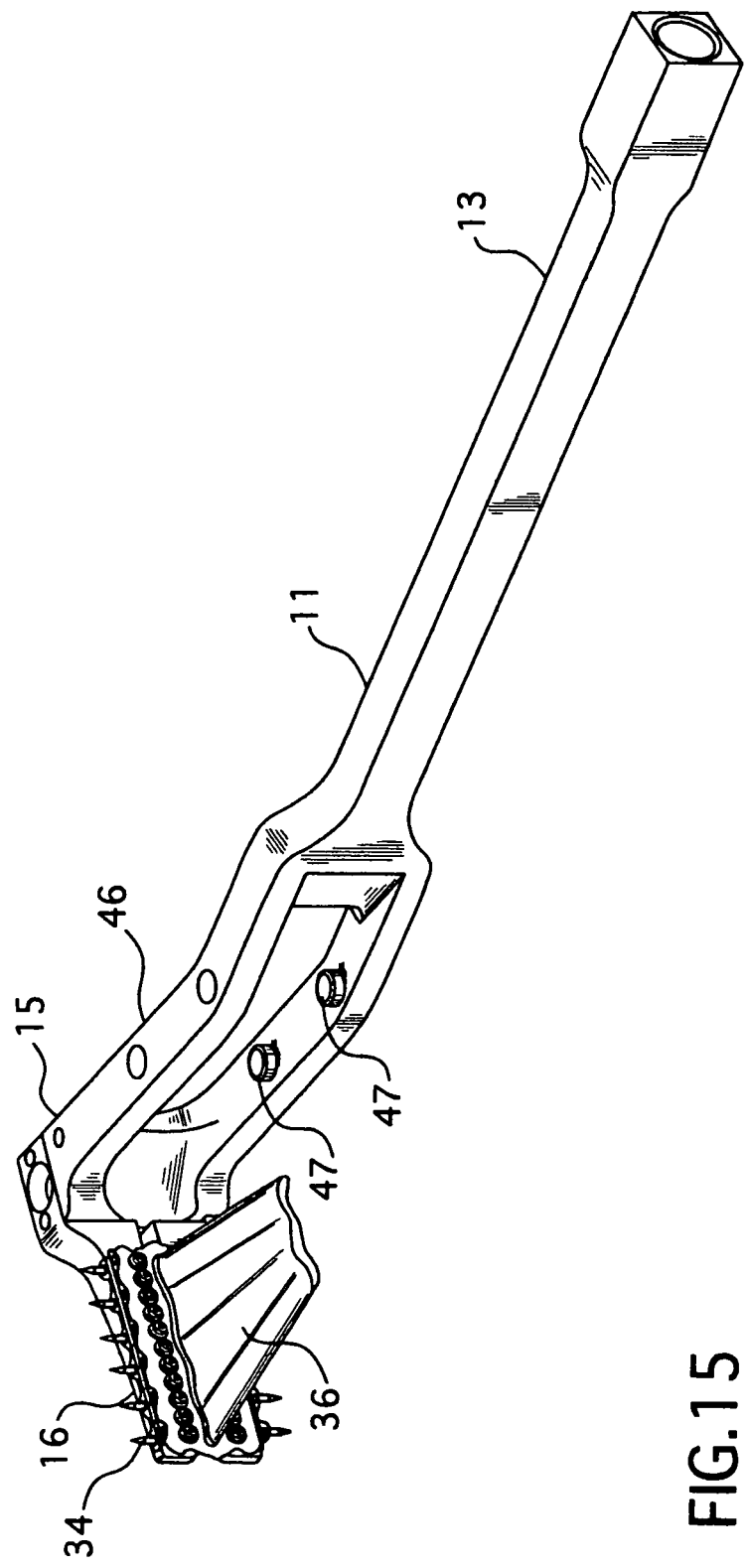
FIG. 15 is a perspective view of the L-shaped clip retainer tool after stapling of the hollow organ ends together and with the L-shaped staple retainer tool removed.

FIGS. 7 through 11 illustrate the L-shaped clip retaining tool 11 and the L-shaped staple retainer tool 12 in combined form in preparation for stapling the respective hollow organ ends 35 and 36 together. FIGS. 12, 13 and 14 illustrate the combined L-shaped clip retainer tool 11 and L-shaped staple retainer tool 12 subsequent to firing or actuation of the stapling apparatus 10, thereby illustrating the hollow organs 35 and 36 in a stapled condition.

A clamp 40 for clamping the two tools 11 and 12 together (see FIGS. 1, 2 and 8) is provided in the form of a clamp rod 41 which has a clamp knob 42 secured to its upper end which is threadably received in the top end 43 of handle 13. Threaded stem 44 of knob 42 is threadably received in female threaded socket 45 of top end 43.

Handle 13 of L-shaped clip retainer tool 11 is provided with a forked or bifurcated bottom end 46 which has opposed sets of guide pins 47 protruding inwardly on the insides of the bifurcated portion 46.

These guide pins 47 are respectively received in side guide slots 48 of the bifurcated base 49 of L-shaped staple retainer tool 12. In this manner the bifurcated base portion 49 of L-shaped staple retainer tool 12 may be inserted between the bifurcations of bottom end 46 of L-shaped clip retainer tool 11 by sliding guide slots 38 downwardly over guide pins 47 so that the L-shaped clip retainer tool 11 and L-shaped staple retainer tool 12 are coupled together with an open ended guided sliding connection whereby the staples 31 are positioned in stapling registration with and over respective of the staple retaining clips 21 of clip retainer 20, and the respective organ exit gaps 17 and 27, of the respective tools are aligned. The bottom face 28 of staple retaining jaw 26 is thus aligned with and positioned in stapling registration over top face 22 of clip retaining jaw 16. In order to retain the two tools 11 and 12 in this coupled fashion as illustrated in FIGS. 7 through 14, the bottom end 48 of clamp rod 41 is engaged against the top surface 49 of jaw stem 58 by turning clamp knob 42 clockwise in threadable engagement down into threaded socket 45 at the top end 43 of handle 13.

Once the two L-shaped tools 11 and 12 are thus combined with the respective hollow organ ends 35 and 36 secured thereto as illustrated in FIGS. 7 through 11, the staple apparatus 10 may be fired or actuated by simultaneously driving the staples 31 downwardly by the downward driving force of driving piston 54 which is provided with multiple staple driving pins 51 that are received respectively in staple sockets 52. The drive pins 51 of driving piston 54 thus engage the exposed heads or top ends 53 of staples 31 to thereby simultaneously drive all staples 31 downwardly through organ tissue of coaptated hollow organ ends 35 and 36. This stapling actuation is caused by forcing staple push rod 60 downwardly against the top surface 58 of piston stem 50 which is rigidly secured with staple driving piston 54. A driver in the form of driver knob 63 is threadably secured to the upper end 65 of drive rod 60 and is threadably received at 64 in the upper end 65 of staple retainer handle 12. When staple firing knob 63 is turned clockwise, firing rod 60 is forced downwardly against the top surface 49 of stem 50 to simultaneously force all staples 31 downwardly with staple piston 54 for simultaneous penetration into and with underlying corresponding staple retaining clips 21 in underlying clip retainer 20.

Stapling Procedure

With reference to the drawings, the procedure for stapling hollow organ ends 35 and 36 together will be described.

First, with reference to FIGS. 1 and 1A, the retaining clips 21 are respectively loaded into their respective pockets on clip retainer 20. Then referring next to FIGS. 4 and 4C, the firing drive rod 60 is adjusted by manipulation of knob 63 and direct manipulation also of stem 50 (FIG. 8) so that the stapler piston 54, together with stem 50, is positioned in the load position as indicted by the indicator 70. When the indicator 70 indicates that the stapling piston 54 is in the load position, the staples 31 are inserted into their respective sockets 30, together with their surrounding bushings 33, as best illustrated in FIGS. 10 and 11.

Then hollow organ end 35 is connected to the staple clip retainer foot 16 by placing it through the C slot in the C-shaped jaw 16 and attached to the holding pins 34 as illustrated in FIGS. 5 and 5D. Then the other hollow organ end 36 is connected to the foot 24 of the staple retaining tool 12 by placing it through the center opening of the C-shaped foot 24 and attaching it to the holding pins as illustrated in FIGS. 6 and 6E.

Thereafter, staple retaining tool 12 with its attached hollow organ end 36 is slidably guided into combination with clip retaining tool 11, together with its applied organ end 35, as previously described and disclosed and clamp rod 41 is then inserted into the top of handle 13 to engage the top surface 49 of stem 50 for staple driving piston 54, and knob 42 is rotated clockwise in its threaded socket 45 to securely clamp stapling foot 24 in stapling registration with clip retaining foot 16.

Accordingly, the two tools 11 and 12 are clamped together with the organ ends 35 and 36 respectively applied and with the two tools in stapling registration whereby firing actuation of the stapling apparatus 10 is ready.

Next, the stapling actuation or firing knob 63 is rotated clockwise to push drive rod 60 downward against stem 50 of stapling piston 54 until indicator 70 indicates that piston 54 has been forced downward to a sufficient extent to staple the two organ ends 35 and 36 together as illustrated in FIGS. 12, 13 and 14. When this occurs the stapler piston 54 has driven the staples 31 through the hollow organ ends 35 and 36 as indicated in FIGS. 12 through 14.

After complete stapling, the clamp rod 41 is removed to disengage clamping engagement between the tools 11 and 12. Then the hollow organ end 36 is cut to free it from the holding pins 34. Thereafter the stapling knob 63 is turned further clockwise to completely eject the bushings 33 from their respective staple sockets 52.

Figure 16:
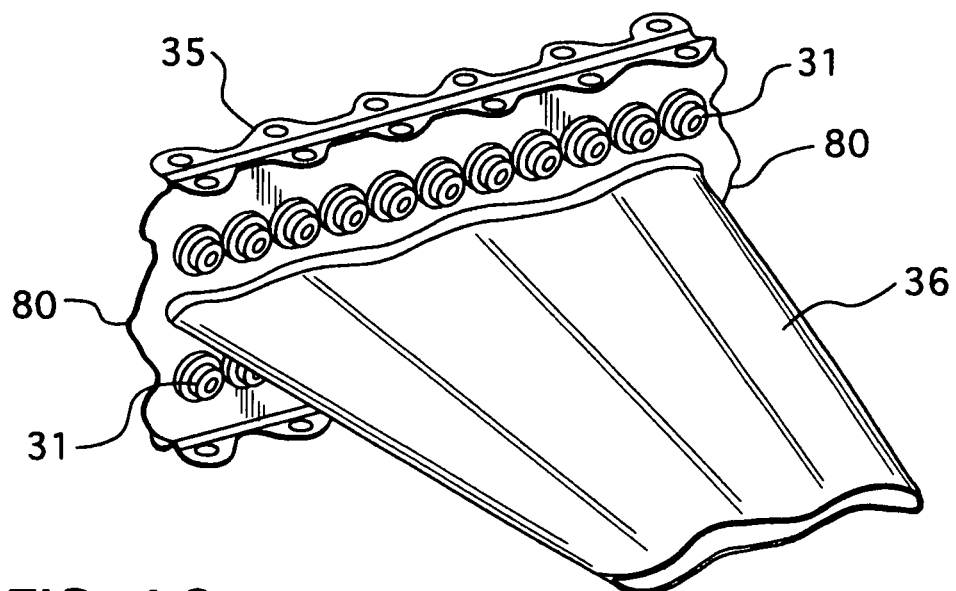
FIG. 16 is an enlarged perspective view of the anastomosis organ ends removed from the L-shaped retainer tool of FIG. 15.
Figure 17:
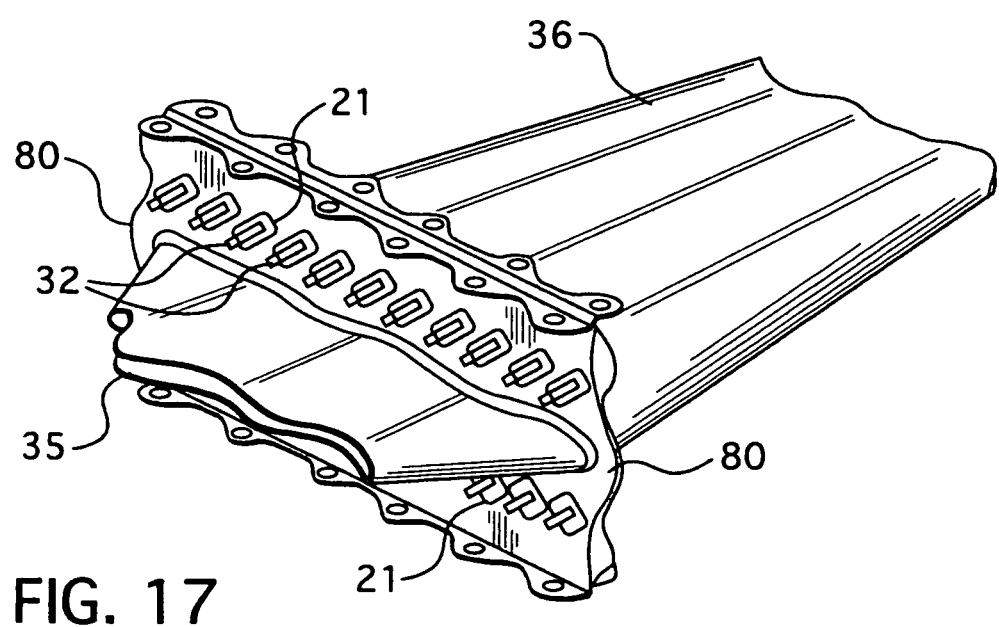
FIG. 17 is a perspective view of the anastomosis hollow organ ends shown in FIG. 16 from the reverse side.

L-shaped staple retainer tool 12 is then removed from tool 11 and also from organ end 36 through gap 27 of the tool, and in the same manner organ end 35 is cut from pins 34 and the jaw of tool 11 is removed from organ end 35 through the gap 17 thereof leaving the anastomosed hollow organ ends as seen in FIGS. 16 and 17. Additional hand sutures may be necessary at the opposite ends 80 of the connected hollow organ ends 35 and 36.

Prior to any given operation, a more than adequate number of stapling apparatus 10 will be preloaded, sterilized and ready for use.

Two important advantages of the stapling apparatus 10 of the present invention is the fact that the L-shaped configuration of the tool provides excellent unobstructed access to the surgical site where the anastomosis is to be performed. In addition, the L-shaped configuration of the stapling apparatus 10 permits reliable failsafe actuation of all staples and failsafe actuation of the stapler mechanism because the L-shaped configuration permits the staple driving mechanism to be actuated from the handles of the tool whereby uniform stapling pressure may be applied downwardly and simultaneously on all staple heads more than adequate with applied stapling pressures. This is unlike stapling apparatus of the prior art which cannot apply stapling pressure initiated in line with the staples. In prior art stapling devices the stapling pressures are generally initially applied by a slide type stapling mechanism that progressively slides over the staple heads and a ramped surface thereof progressively applies stapling pressure to the staple heads (see Tzakis U.S. Pat. No. 5,188,638), or by arcuately applied pressures in a clamp type mechanism wherein the clamp jaws are positioned in planes that are axially aligned with the axis of the tool actuator handle (see U.S. Pat. No. 4,917,090), instead of being positioned in planes that are transverse to the handle axis.

Alternative Embodiments

The embodiment described above is a preferred example of the stapling instrument of the present invention, and there are other possible alternative embodiments which are encompassed by the present invention and the following claims.

Figure 18:
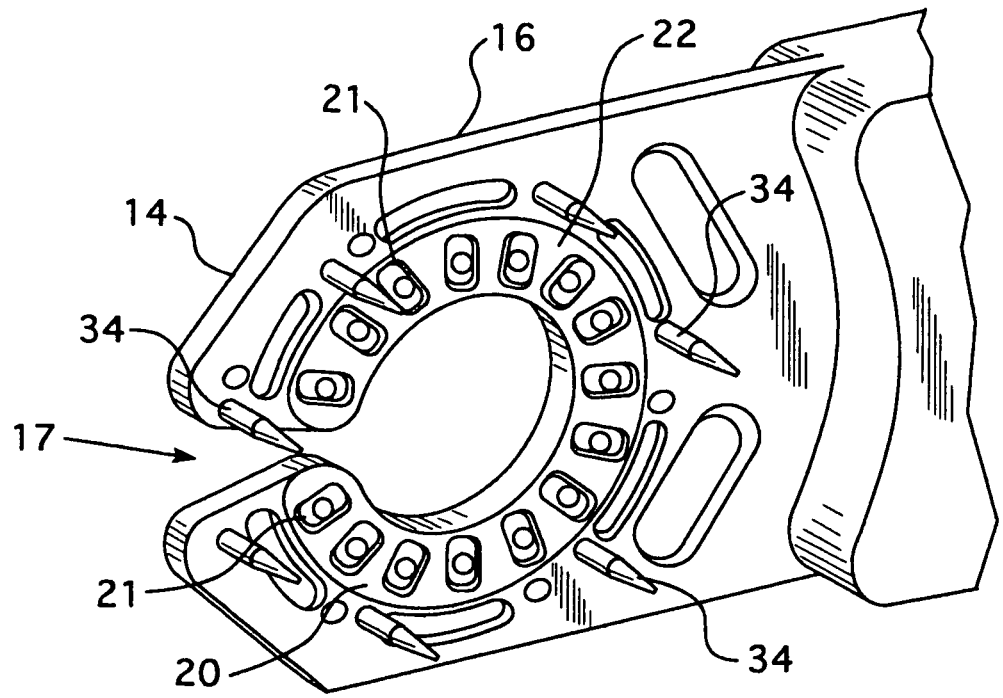
FIG. 18 is a perspective view of the clip retaining foot of the L-shaped clip retainer tool shown in FIG. 1 illustrating another embodiment of the anastomosis stapler of the present invention.

For example, the configuration of the C-shaped clip jaw 16 and the C-shaped staple jaw 24 need not be of a flat configuration as illustrated in the previous figures. The jaws 16 and 24 may take on an oval configuration or even a round configuration as illustrated in FIG. 18 wherein the C-shaped clip jaw 16 is shown to be circular and to contain a circular shaped clip retainer 20. Like elements are designated with the same reference numerals.

Figure 19:
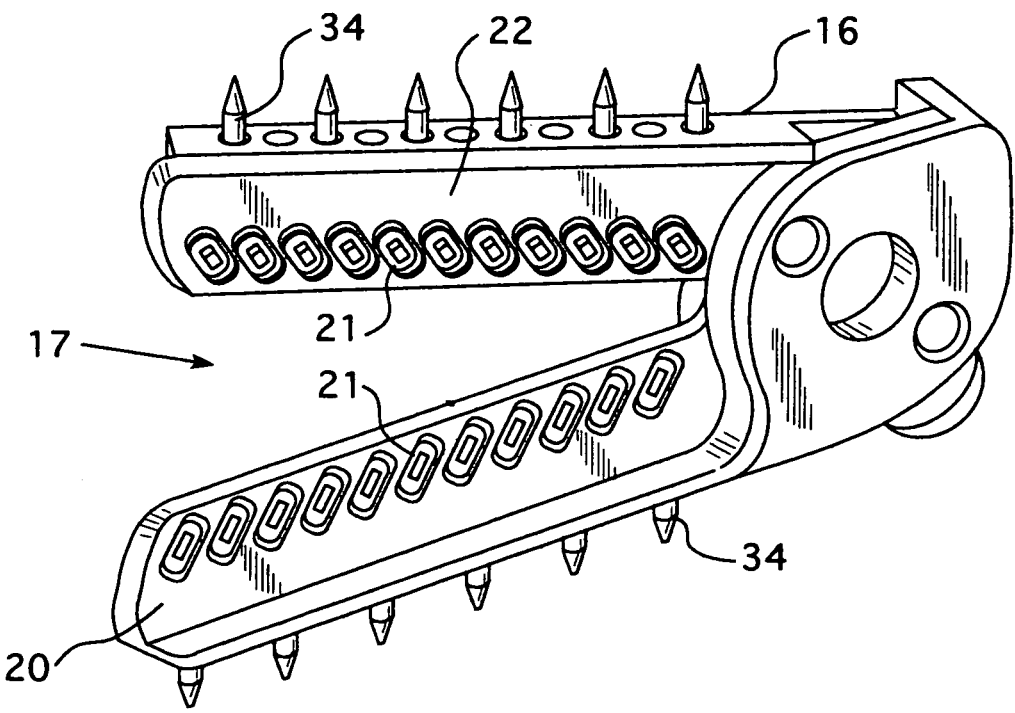
FIG. 19 is a perspective view of yet a further embodiment of the clip retaining foot portion of the C-shaped clip jaw for the L-shaped clip retainer tool shown in FIG. 1.

In addition, as illustrated in FIG. 19, the C-shaped clip and staple jaws 16 and 26 may also be pivotal as illustrated whereby the jaws may be opened and closed to provide better ingress and egress of the hollow organ ends prior to stapling and subsequent to stapling.

Also, in the principal embodiment described, each of the staple retaining clips 21 and each of the corresponding staples 31 are independent. In other words, the staple retaining clips 21 are not connected to each other, and the staples 31 are not connected to each other. Accordingly, after the anastomosis process has been completed, the respectively secured staples 31 and clips 21 may be rearranged to the natural annular configuration of the hollow organ ends which are secured together. However, because of the C-shaped configuration of the clip retainer 20 and the staple retainer 30, this generally necessitates the use of additional hand sutures at the opposite ends of the anastomosis as indicated at 80 in FIGS. 16 an 17.

In order to avoid the necessity of these additional sutures 80, the staple retainer 20 may be provided in the form of a continuous annular ring whereby each of the staple retaining clips 21 is an integral part of the clip retainer ring 20 such that all the staple retainer clips 21 are interconnected as part and parcel of the clip retainer ring 20. Similarly, the staple retainer ring 29 may also consist of a continuous annular ring receiving the staples 31 therein in respective sockets whereby the staple retainer ring 29 is permanently stapled to the staple clip retaining ring 20 with the stapled hollow organ ends 35 and 36 sandwiched therebetween.

In this latter described embodiment, the staple retaining ring 29 and the clip retaining ring 20 remain as permanent part of the anastomosis of hollow organ ends 35 and 36 in the same manner the fastening means 5a and 5b of U.S. Pat. No. 4,917,090 remain part of the anastomosis connection. Also, with this latter described embodiment, the respective annular clip retaining ring and staple retaining rings 20 and 29 of the present invention are slidably removable through the end gaps 17 and 27 of the respective jaws 16 and 26 in the same manner that clamp fastening means 5a and 5b are removable from the their respective C-shaped jaws 2 and 3, best illustrated in that patent in FIGS. 1, 2 and 5. Accordingly, the retainer rings 20 and 29 of the present invention may take on the same configuration and function as the fasting means 5a and 5b, and the jaws 16 and 26 of the stapling apparatus 10 of the present invention may take on the configuration of the jaw like elements 2 and 3 in U.S. Pat. No. 4,917,090. Accordingly, the content and description of U.S. Pat. No. 4,917,090 is incorporated herein by reference in their entirety to illustrate this possible alternative embodiment.

The staples 31 may also take on a different configuration than the staple nails disclosed. For instance, the staples 31 may take on a U-shaped configuration as conventional staples. Also, the staple retainer clips 21 may take on a different configuration than the push nut type illustrated. For example, the retaining clips may be simply small solid plastic blocks which are not perforated and which retain the tips of staples therein by penetration of the staple tips. To provide more secure attachment in this configuration, the staple tips may be ribbed so that once they penetrate the solid staple retaining blocks they are not easily removed and thereby remain secured.

Referring next to the embodiment illustrated in FIGS. 20, 21, 22 and 23, another embodiment of the stapling apparatus 10 of the present invention is illustrated. In this embodiment, the clip jaw 16 and the staple jaw 26 are pivotal from a normally closed position for stapling to an open loading position for providing easy and unobstructed loading and unloading of the hollow organ tissue ends. In addition, an alternative mechanism for clamping the two tool bodies 11 and 12 together and for actuating the stapling mechanism is illustrated. Like elements are designated with the same reference numeral.

Figure 20:
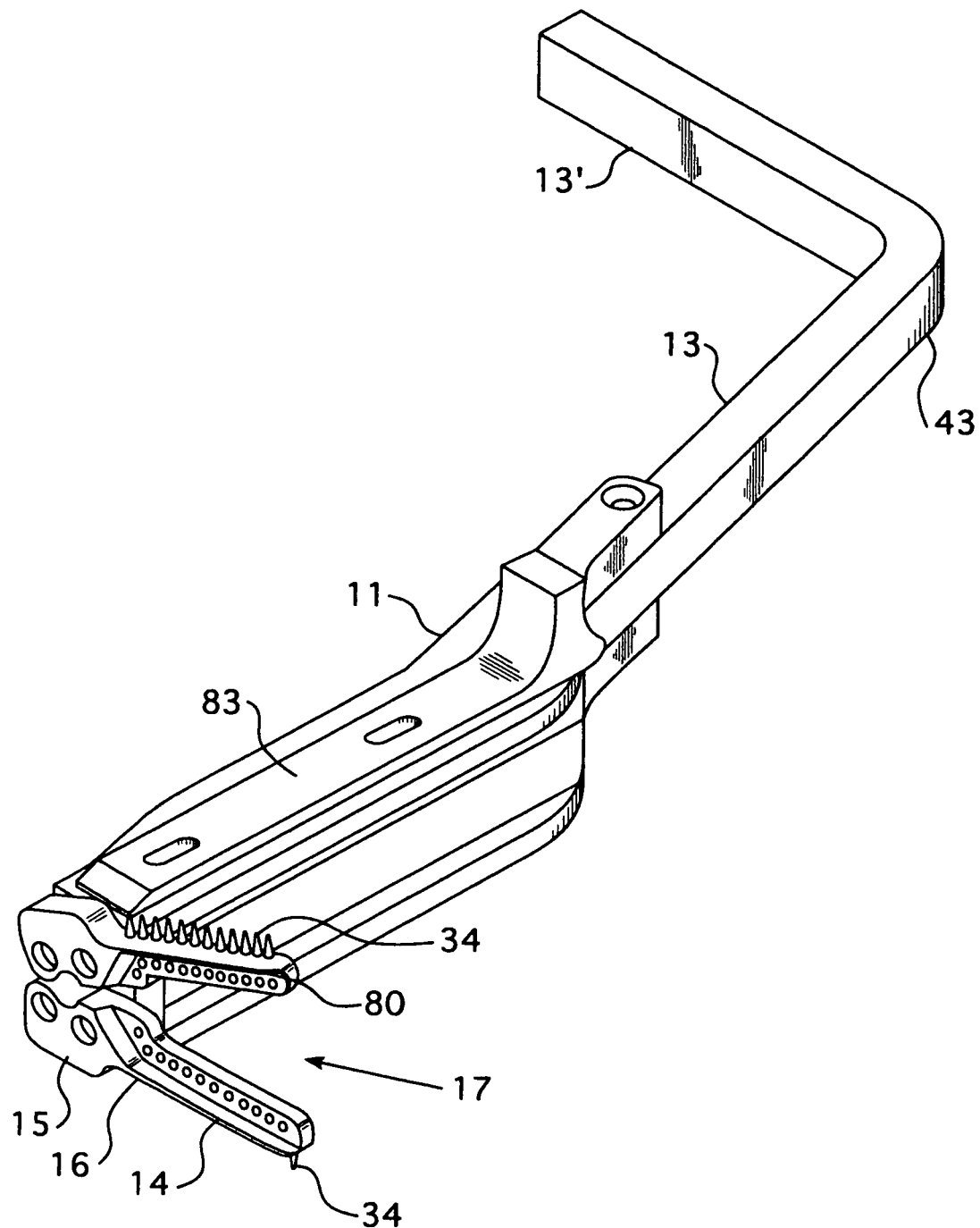
FIGS. 20, 21, 22 and 23 are perspective views illustrating another embodiment of the stapling apparatus of the present invention incorporating pivotal jaws for loading and unloading of hollow organ tissue ends and a modification of the staple actuation mechanism.
Figure 21:
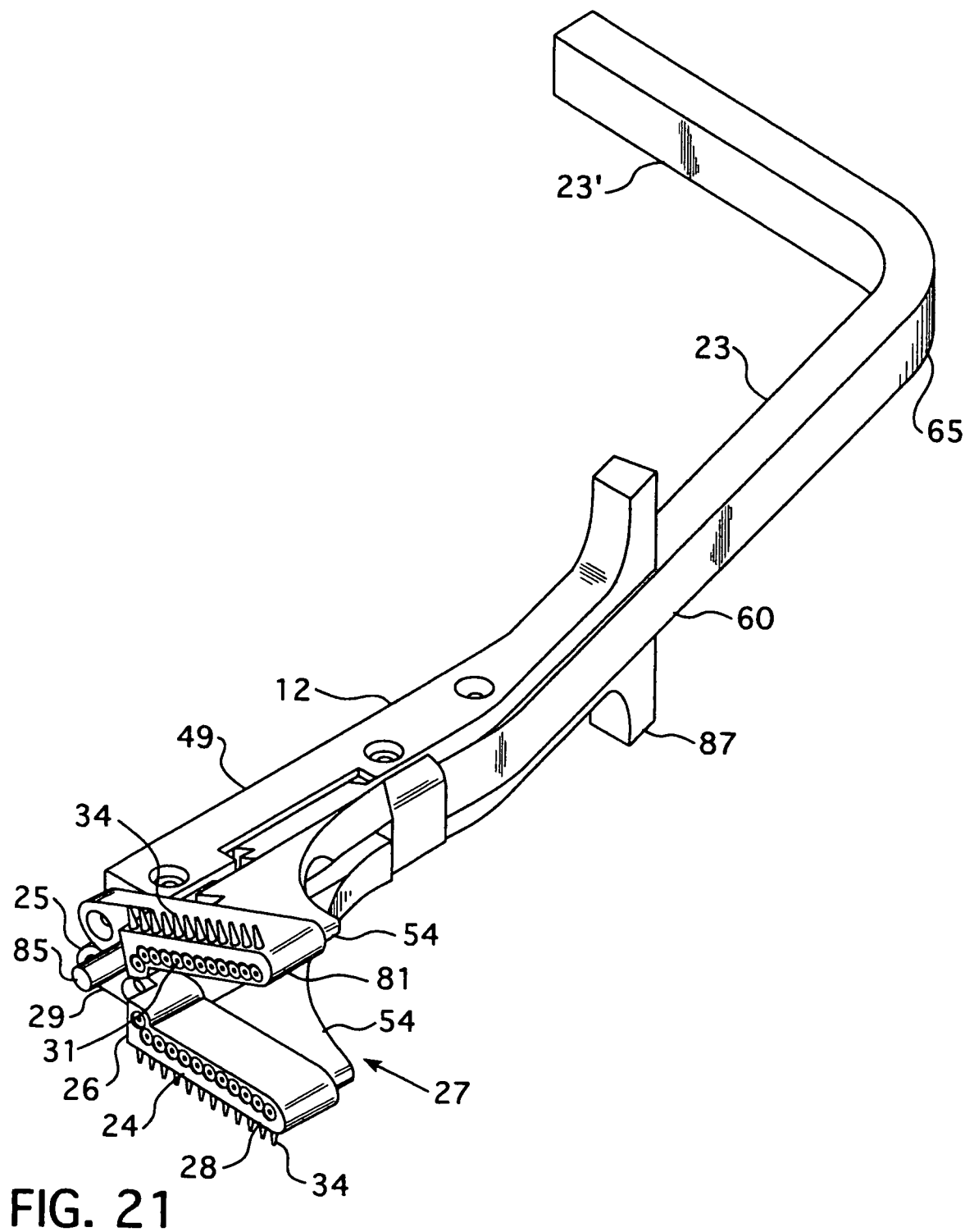

In this embodiment, the right hand jaw arm 80 of the clip retainer jaw 16 and the right hand jaw arm 81 of the staple jaw 26 are pivotal outward at their respective bases as indicated respectively in FIGS. 20 and 21. This permits unobstructed initial ingress and final egress of hollow organ tissue ends 35 and 36 for loading and unloading before and after stapling.

Figure 22:
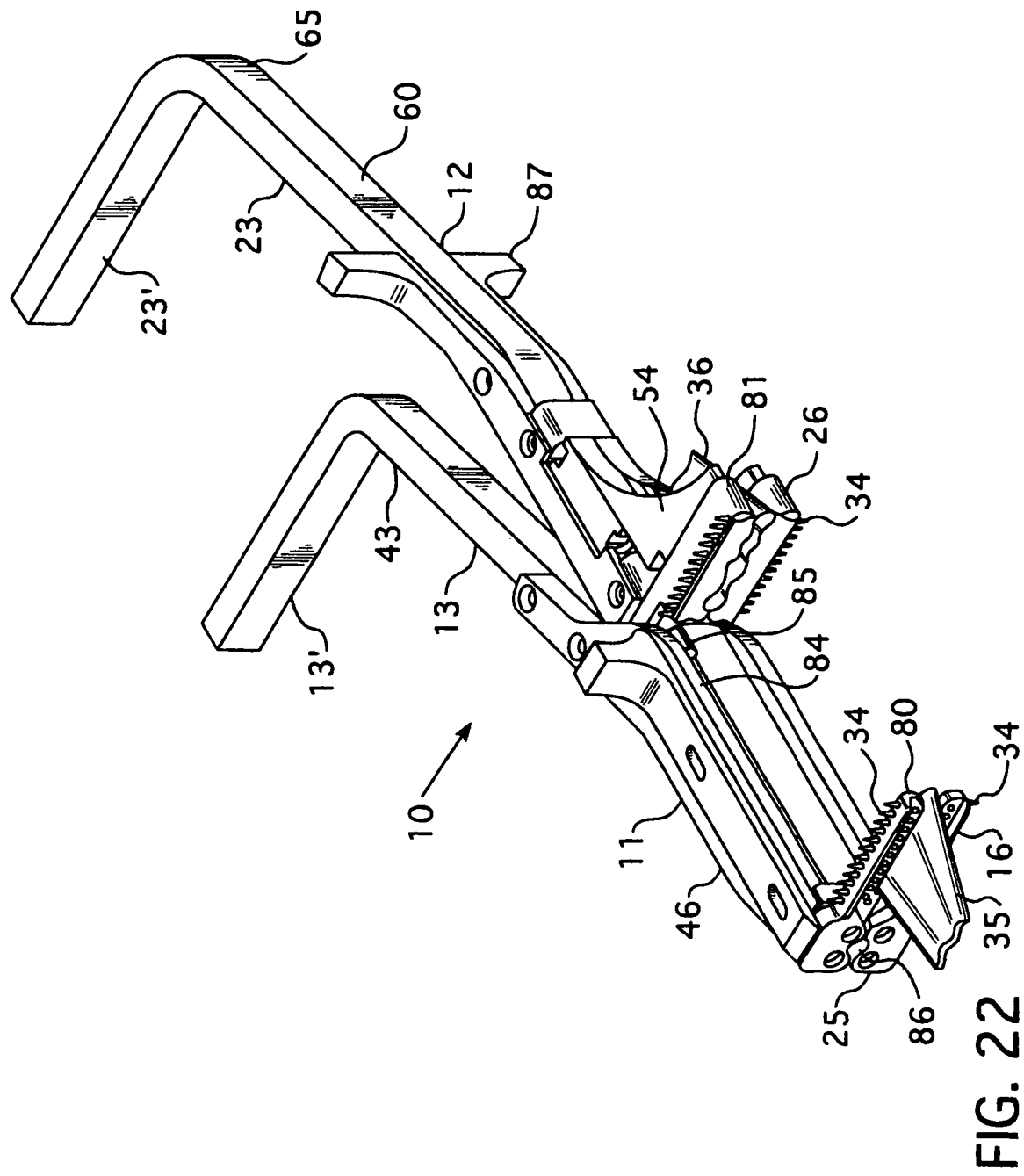
Figure 23:
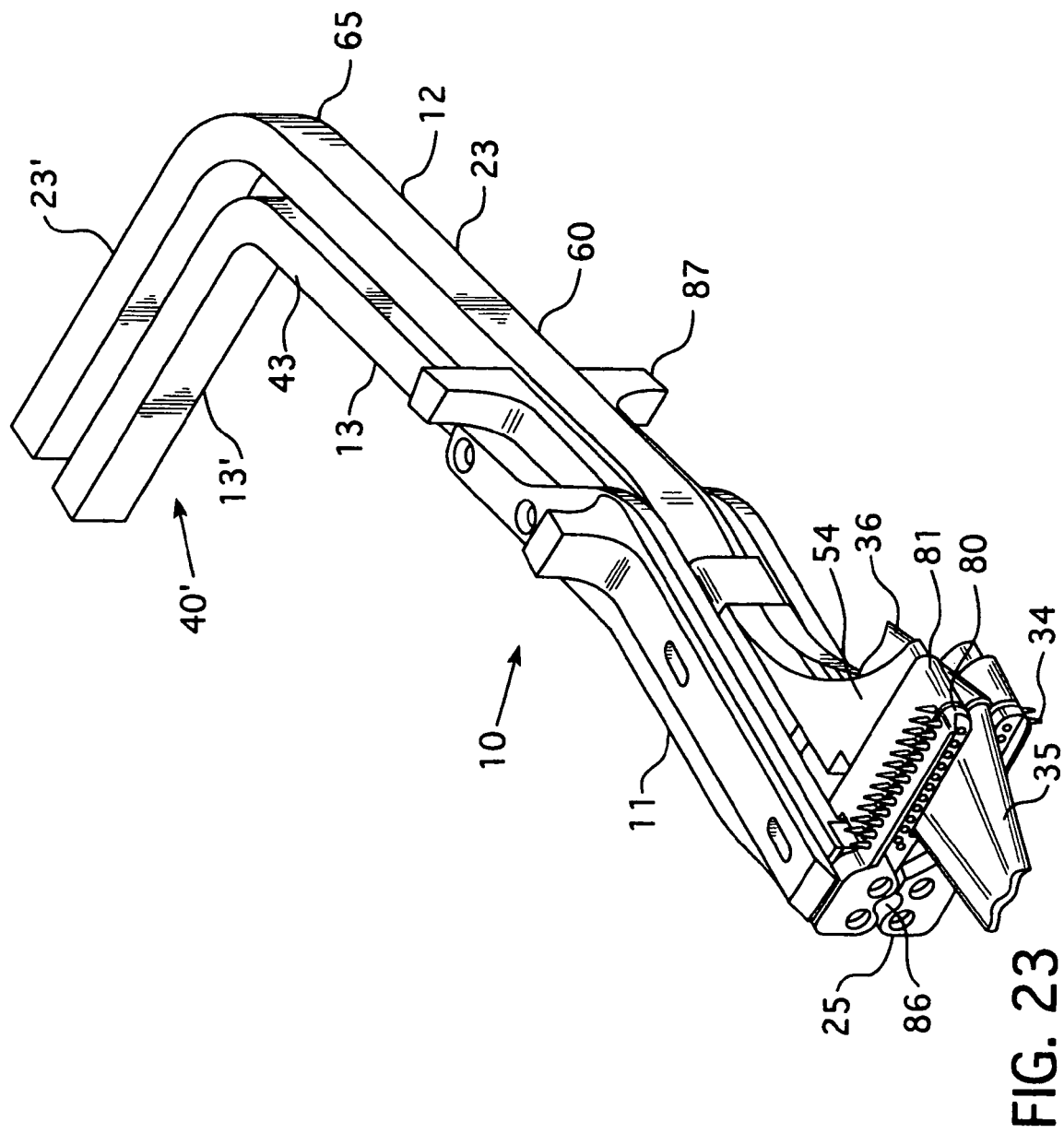
Figure 24:
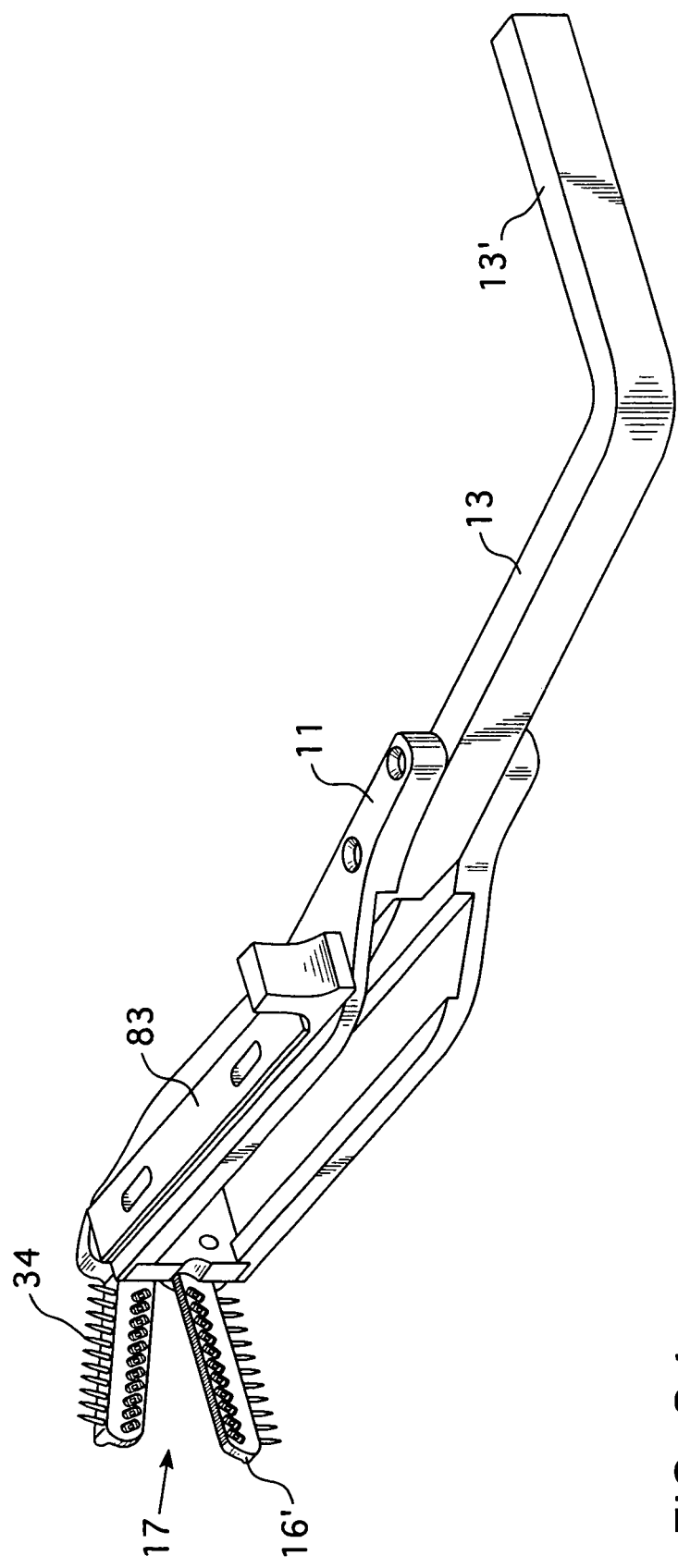
FIGS. 24, 24A, 25, 25A, 26 and 27 are perspective views illustrating yet another embodiment of the stapling apparatus of the present invention incorporating hemostat pivotal jaws for retaining and clamping respective hollow organ ends prior to stapling.
Figure 25:
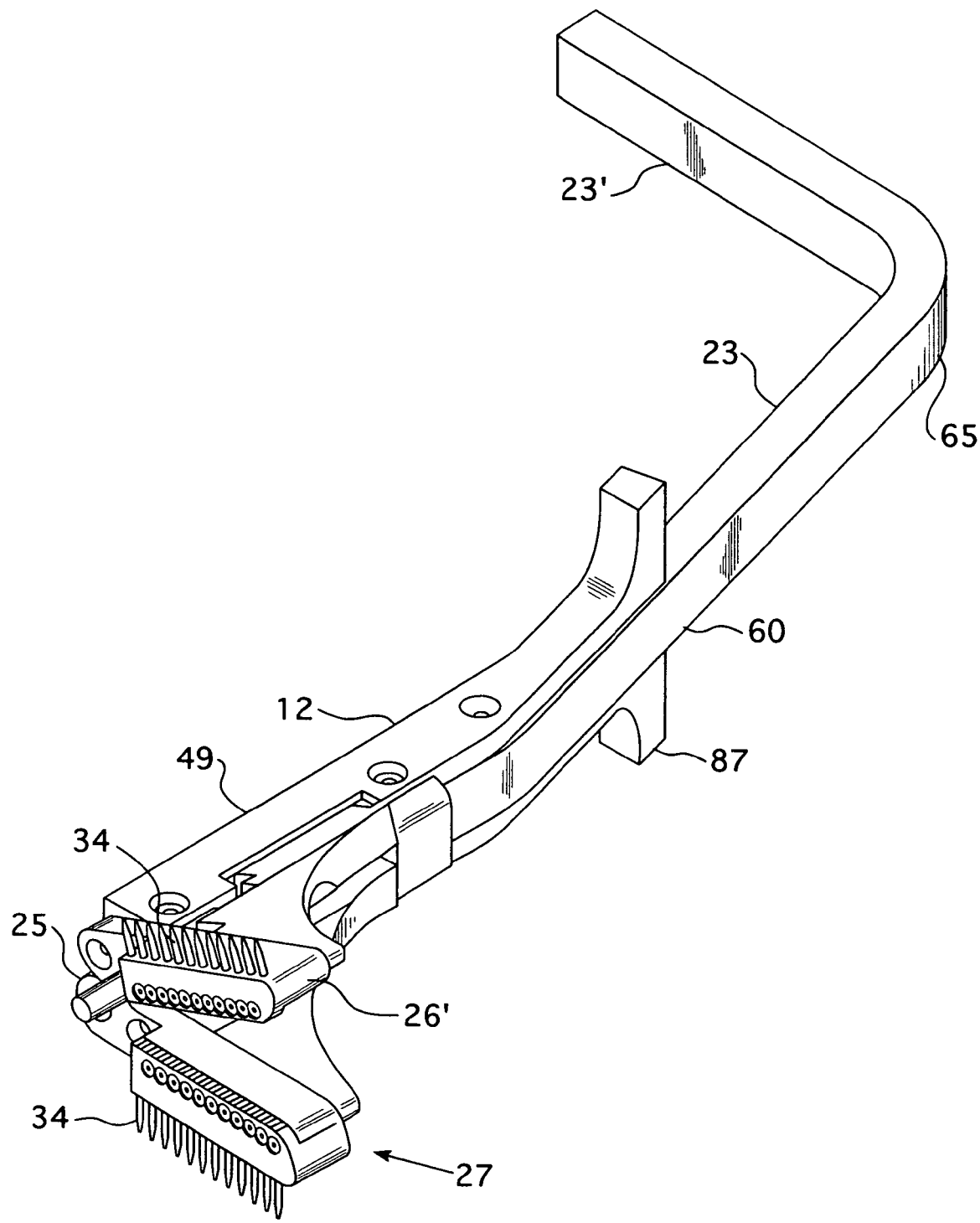
Figure 24A:
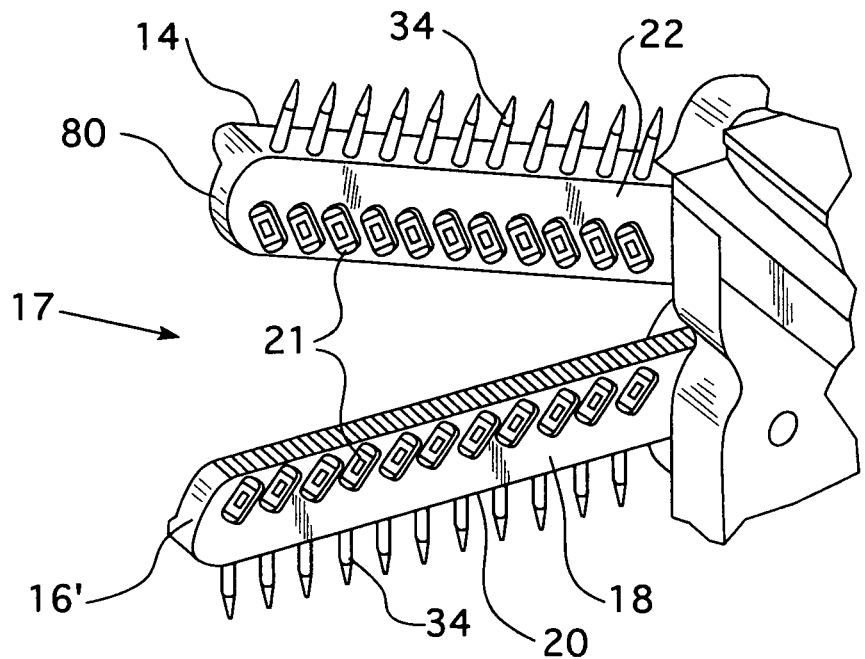
Figure 25A:
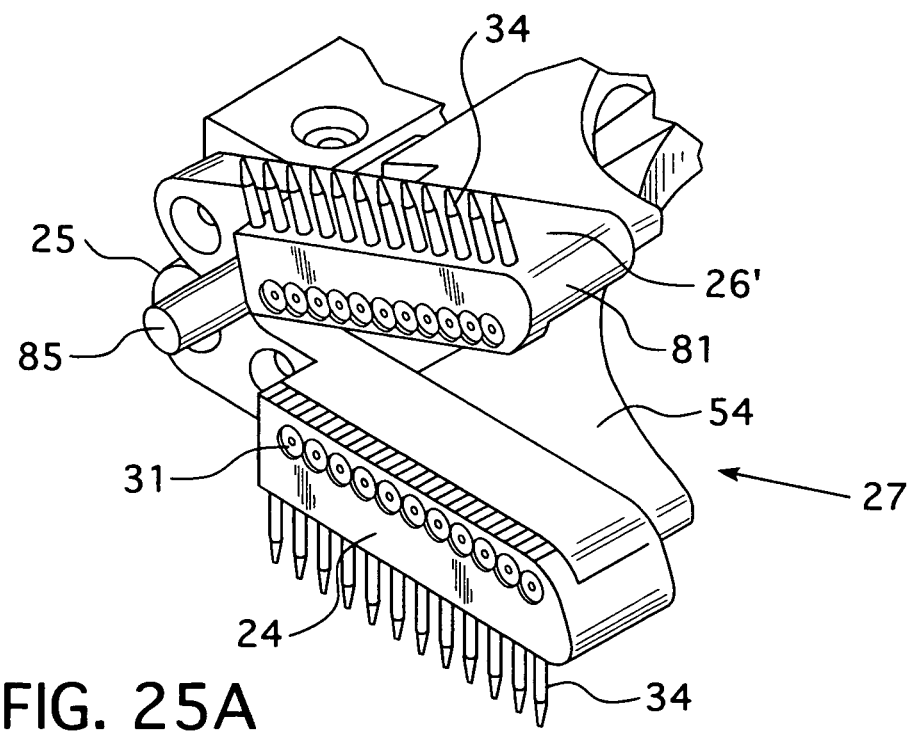
Figure 26:
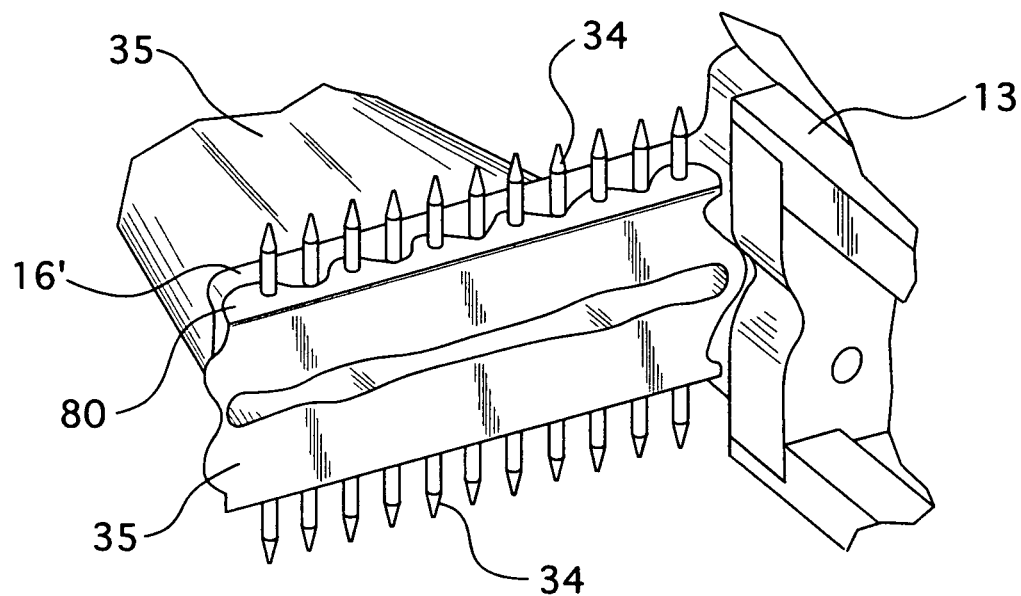
Figure 27:
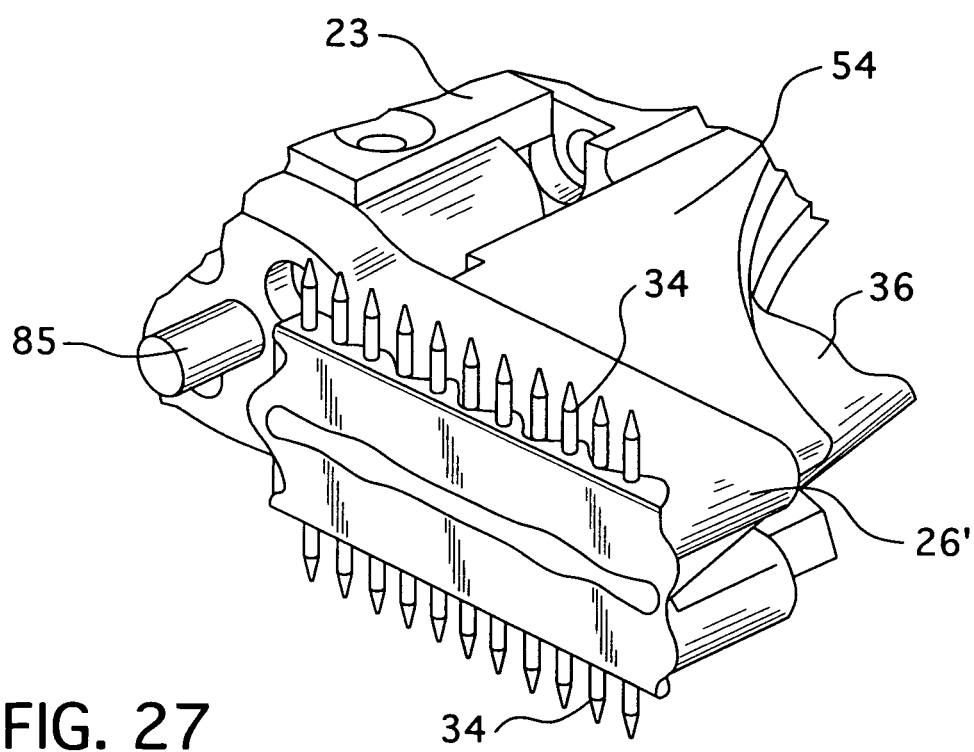

Slide lock 83 is slidable along handle 13 to an open position as indicated in FIG. 20 to prevent jaw arm 80 to pivot outward, and then slide lock 83 is slidable down the handle 13 to a closed position as indicated in FIGS. 22 and 23 to engage and maintain the clip jaw 16 in its normally closed position. Similarly, arm 81 of staple jaw 26 may be maintained in a closed position by the slide lock 84 provided by the side arm of clip retainer tool 11 when staple retainer tool 12 is slidably inserted downwardly into clip retaining tool 11 from the initial point of insertion as illustrated in FIG. 22 to the final position of insertion illustrated in FIG. 23. Accordingly, the slide lock 84 prevents jaw arm 81 from reopening. In order to maintain staple retainer 12 in registered stapling alignment with clip retaining tool 11, the bottom end of staple retainer tool 12 is provided with a downwardly protruding stud 85 received in guide retaining aperture 86 in the bottom end of clip retaining tool 11.

In this embodiment, the clamp 40 designated in the previous embodiments operates in an entirely different manner in this embodiment and the clamp is therefore designated as clamp 40' in this embodiment. In this embodiment, the retainer handles 13 and 23 have spaced upper handle ends 13' and 23' respectively which adjacently extend together, with the staple handle end 23' positioned above the clip retainer handle end 13', in a transverse direction respectively from upper proximal ends 43 and 65 of handles 13 and 23. This arrangement accordingly provides handle ends 13' and 23' for grasping and clamping together whereby the tools are clamped together by one's hand in stapling registration to provide the clamp 40'.

Also, in this embodiment, stapling by the apparatus 10 is actuated by further squeezing the handle ends 13' and 23' together, instead of using the threaded knob mechanism of the previous embodiment.

In this embodiment, the staple firing rod 60 is provided by the staple retainer handle 23 itself. Thus when handle ends 13' and 23' are squeezed together by hand manipulation, this causes staple retainer handle 23 to move downwardly relative to handle 13 of the clip retainer tool 11, and of bottom end of handle 23 in turn pushes downwardly on staple driving piston 54 thereby causing stapling of the hollow organ ends 35 and 36 together as previously described. When the stapling operation is completed, staple retainer release 87 is grasped by the hands of the operator and pulled upwardly relative to staple retainer handle 23 to fully release the staple heads from staple retainer 32 in order to fully release stapler tool 12 for removal from clip retaining tool 11 without disturbing the stapled ends 35 and 36 of the hollow organ ends.

Referring next to FIGS. 24 through 27, the embodiment illustrated is identical in construction and operation as the stapler apparatus illustrated in FIGS. 20 through 23, with the exception that the hinged jaws 16 and 26 provide hemostat jaws 16' and 26' which close to clamp the respective organ ends 35 and 36 in the same manner that a conventional hemostat clamps. Accordingly, the elements of FIGS. 24 through 27 are identically numbered, with the exception that spaced pivotal jaws 16 and 26 are respectively renumbered as hemostat jaws 16' and 26'.

Hemostat jaws 16' and 26' permit the surgeon to attach the respective hollow organs ends 35 and 36 to the respective tools 11 and 12 prior to assembly of the tools for stapler registration. In addition, in a situation where the hollow organs to be stapled are vascular, the hemostatic attachment of the blood vessels to the respective tools 11 and 12 stops the flow of blood during the stapling procedure.

We claim:

1. A stapling apparatus for performing anastomosis on hollow organ ends, comprising:
   - an adjacent aligned pair of stapling tools combinable to form the stapling apparatus, the tools each having stapling jaws depending from respective interconnected tool handles, and said stapling jaws positioned in aligned registration when said stapling tools are combined for stapling hollow organ ends positioned between said jaws together to form an anastomosis;
   - said stapling tools including a stapling mechanism for stapling together hollow organ ends positioned between said aligned stapling jaws;
   - each of said stapling jaws respectively including opposing hinged hemostat jaws adjacently secured to said stapling jaws and operable for clamping respective hollow organ ends therebetween prior to stapling;
   - said pair of stapling tools combinable and fully separable from each other at said interconnection of said handles for guided manipulation into and out of stapling registration by means of guide slots sliding over guide pins.

2. The stapling apparatus of claim 1, including a clamp for temporarily clamping said stapling tools together with said stapling jaws in stapling registration.

3. The stapling apparatus of claim 1, said stapling jaws having a spaced series of pins extending from said stapling jaws for piercing and retaining the respective clamped hollow organ ends stretched over said stapling jaws for stapling.

4. The stapling apparatus of claim 3, said pins extending outward from outer sides of said stapling jaws.

* * * * *